United States Patent
Kumar et al.

(10) Patent No.: US 10,231,616 B2
(45) Date of Patent: *Mar. 19, 2019

(54) SYSTEMS AND METHODS FOR SUB-APERTURE BASED ABERRATION MEASUREMENT AND CORRECTION IN INTERFEROMETRIC IMAGING

(71) Applicant: Carl Zeiss Meditec, Inc., Dublin, CA (US)

(72) Inventors: Abhishek Kumar, Vienna (AT); Alexandre R. Tumlinson, San Leandro, CA (US); Rainer Leitgeb, Vienna (AT)

(73) Assignee: CARL ZEISS MEDITEC, INC., Dublin, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/683,572

(22) Filed: Aug. 22, 2017

(65) Prior Publication Data

US 2018/0035883 A1    Feb. 8, 2018

Related U.S. Application Data

(63) Continuation of application No. 14/758,792, filed as application No. PCT/EP2014/051918 on Jan. 31, 2014, now Pat. No. 9,775,511.

(Continued)

(51) Int. Cl.
*G01N 21/17* (2006.01)
*A61B 3/10* (2006.01)
(Continued)

(52) U.S. Cl.
CPC ............ *A61B 3/102* (2013.01); *A61B 3/0025* (2013.01); *A61B 3/1015* (2013.01); *A61B 3/14* (2013.01);
(Continued)

(58) Field of Classification Search
CPC ... G01B 9/02085; A61B 3/102; G03H 1/0866
See application file for complete search history.

(56) References Cited

U.S. PATENT DOCUMENTS 5,854,602 A   12/1998   Stankwitz et al.
6,724,464 B2   4/2004   Yang et al.
(Continued)

FOREIGN PATENT DOCUMENTS

EP        1626257 A1    2/2006
JP     2002-202220 A    7/2002
(Continued)

OTHER PUBLICATIONS

Adie et al., "Computational Adaptive Optics for Broadband Optical Interferometric Tomography of Biological Tissue", PNAS, vol. 109, May 8, 2012, pp. 7175-7180.

(Continued)

*Primary Examiner* — Jonathan M Hansen
(74) *Attorney, Agent, or Firm* — Morrison & Foerster LLP

(57) ABSTRACT

Systems and methods for sub-aperture correlation based wavefront measurement in a thick sample and correction as a post processing technique for interferometric imaging to achieve near diffraction limited resolution are described. Theory, simulation and experimental results are presented for the case of full field interference microscopy. The inventive technique can be applied to any coherent interferometric imaging technique and does not require knowledge of any system parameters. In one embodiment of the present application, a fast and simple way to correct for defocus aberration is described. A variety of applications for the method are presented.

30 Claims, 8 Drawing Sheets

Related U.S. Application Data

(60) Provisional application No. 61/777,090, filed on Mar. 12, 2013, provisional application No. 61/759,854, filed on Feb. 1, 2013.

(51) Int. Cl.

| | | |
|---|---|---|
| *G01N 21/47* | (2006.01) | |
| *G03H 1/08* | (2006.01) | |
| *G03H 1/04* | (2006.01) | |
| *A61B 3/00* | (2006.01) | |
| *A61B 3/14* | (2006.01) | |
| *G03H 1/00* | (2006.01) | |

(52) U.S. Cl.
CPC ......... *G01N 21/4795* (2013.01); *G03H 1/041* (2013.01); *G03H 1/0866* (2013.01); *G01N 2021/1787* (2013.01); *G03H 2001/005* (2013.01); *G03H 2001/0083* (2013.01); *G03H 2001/0452* (2013.01); *G03H 2001/0883* (2013.01); *G03H 2210/30* (2013.01); *G03H 2222/14* (2013.01); *G03H 2222/23* (2013.01); *G03H 2223/52* (2013.01); *G03H 2223/55* (2013.01)

(56) References Cited

U.S. PATENT DOCUMENTS

| | | | |
|---|---|---|---|
| 7,602,501 | B2 | 10/2009 | Ralston et al. |
| 7,659,993 | B2 | 2/2010 | Feierabend et al. |
| 8,102,299 | B2 | 1/2012 | Young et al. |
| 8,123,357 | B2 | 2/2012 | Dai et al. |
| 8,243,353 | B1 | 8/2012 | Gutin et al. |
| 8,471,897 | B2 | 6/2013 | Rodriguez Ramos et al. |
| 8,730,573 | B2 | 5/2014 | Betzig et al. |
| 9,089,281 | B2 | 7/2015 | Yuasa et al. |
| 9,247,874 | B2 * | 2/2016 | Kumar .................. A61B 3/14 |
| 2003/0053028 | A1 | 3/2003 | Wirth |
| 2006/0033933 | A1 | 2/2006 | Feierabend et al. |
| 2007/0258095 | A1 * | 11/2007 | Olivier .................. A61B 3/102 356/479 |
| 2011/0032533 | A1 * | 2/2011 | Izatt .................. G01B 11/2441 356/497 |
| 2011/0134436 | A1 | 6/2011 | Podoleanu et al. |
| 2014/0218684 | A1 * | 8/2014 | Kumar ............... G01N 21/4795 351/206 |
| 2016/0000319 | A1 * | 1/2016 | Kumar ............... G01N 21/4795 351/206 |
| 2018/0035883 | A1 * | 2/2018 | Kumar ............... G01N 21/4795 |

FOREIGN PATENT DOCUMENTS

| | | |
|---|---|---|
| JP | 2010-167253 A | 8/2010 |
| JP | 2012-533069 A | 12/2012 |
| WO | 2012/143113 A1 | 10/2012 |

OTHER PUBLICATIONS

Arons et al., "Use of Fourier Synthesis Holography to Image through Inhomogeneities", Optics Letters, vol. 18, No. 21, Optical Society of America, US, Nov. 1, 1993, pp. 1852-1854.
Beverage et al., "Measurement of the Three-Dimensional Microscope Point Spread Function Using a Shack—Hartmann Wavefront Sensor", Journal of Microscopy, vol. 205, Jan. 1, 2002, pp. 61-75.
Biss et al., "An Adaptive Optics Biomicroscope for Mouse Retinal Imaging", Proc. of SPIE, vol. 6467, 2007, pp. 646703-1-646703-8.
Calloway et al., "Subaperture Autofocus for Synthetic Aperture Radar", IEEE Transactions on Aerospace and Electronic Systems, vol. 30, No. 2, Apr. 1994, pp. 617-621.
Feierabend et al., "Coherence-Gated Wave-Front Sensing in Strongly Scattering Samples", Optics Letters, vol. 29, No. 19, Oct. 1, 2004, pp. 2255-2257.
Franke et al., "High Resolution Holoscopy", Proceedings of SPIE, vol. 8213, 2012, pp. 821324-1-821324-6.
Guizar-Sicairos et al., "Efficient Subpixel Image Registration Algorithms", Optics Letters, vol. 33, No. 2, Jan. 15, 2008, pp. 156-158.
Haist et al., "Scene-Based Wavefront Correction with Spatial Light Modulators", Proc. of SPIE, vol. 7064, 2008, pp. 70640M-1-70640M-11.
Hillman et al., "Common Approach for Compensation of Axial Motion Artifacts in Swept-source OCT and Dispersion in Fourier-domain OCT", Optics Express vol. 20, No. 6, Mar. 12, 2012, pp. 6761-6776.
Hillmann et al., "Efficient Holoscopy Image Reconstruction", Optics Express, vol. 20, No. 19, Sep. 10, 2012, pp. 21247-21263.
Hillmann et al., "Holoscopy-Holographic Optical Coherence Tomography", Optics Letters, vol. 36, No. 13, Jul. 1, 2011, pp. 2390-2392.
Ji et al., "Adaptive Optics via Pupil Segmentation for High-Resolution Imaging in Biological Tissues", Nature Methods, 2009, 30 pages.
Mahajan et al., "Orthonormal Polynomials in Wavefront Analysis: Analytical Solution", J. Opt. Soc. Am. A, vol. 24, No. 9, Sep. 2007, pp. 2994-3016.
Malacara, Daniel, "Optical Testing", Chapter 30: Handbook of Optics, 2nd Edition, 1995, pp. 30.1-30.26.
Marks et al., "Autofocus Algorithm for Dispersion Correction in Optical Coherence Tomography", Applied Optics, vol. 42, No. 16, Jun. 1, 2003, pp. 3038-3046.
Massig, Jurgen H., "Digital Off-Axis Holography with a Synthetic Aperture", Optics Letters, vol. 27, No. 24, Optical Society of America, US, Dec. 15, 2002, pp. 2179-2181.
Nakamura et al., "High-Speed Three-Dimensional Human Retinal Imaging by Line-Field Spectral Domain Optical Coherence Tomography", Optics Express, vol. 15, No. 12, Jun. 11, 2007, pp. 7103-7116.
Pircher et al., "Combining Adaptive Optics with Optical Coherence Tomography: Unveiling the Cellular Structure of the Human Retina In Vivo", Expert Rev. Ophthalmol. vol. 2, No. 6, 2007, pp. 1019-1035.
Platt et al., "History and Principles of Shack Hartmann Wavefront Sensing", Journal of Refractive Surgery, vol. 17, Sep./Oct. 2001, pp. S573-S577.
Poyneer, Lisa A., "Scene-based Shack-Hartmann Wave-Front Sensing: Analysis and Simulation", Applied Optics, vol. 42, No. 29, Oct. 10, 2003, pp. 5807-5815.
Rueckel et al., "Adaptive Wavefront Correction in Two-Photon Microscopy Using Coherence-Gated Wavefront Sensing", PNAS, vol. 103, No. 46, Nov. 14, 2006, pp. 17137-17142.
Rueckel et al., "Properties of Coherence-Gated Wavefront Sensing", J. Opt. Soc. Am. A, vol. 24, No. 11, Nov. 2007, pp. 3517-3529.
Sasaki et al., "Extended Depth of Focus Adaptive Optics Spectral Domain Optical Coherence Tomography", Biomedical Optics Express, vol. 3, No. 10, Oct. 1, 2012, pp. 2353-2370.
Thurman et al., "Phase-Error Correction in Digital Holography", J. Opt. Soc. Am. A, vol. 25, No. 4, Apr. 2008, pp. 983-994.
Tippie et al., "High-Resolution Synthetic-Aperture Digital Holography with Digital Phase and Pupil Correction", Optics Express, vol. 19, No. 13, Jun. 20, 2011, pp. 12027-12038.
Tippie et al., "Sub-Aperture Techniques Applied to Phase-Error Correction in Digital Holography", in Digital Holography and Three-Dimensional Imaging, OSA Technical Digest (CD), paper DMA4, 2011, 3 pages.
Tuohy et al., "Depth-Resolved Wavefront Aberrations using a Coherence-Gated Shack-Hartmann Wavefront Sensor", Optics Express, vol. 18, No. 4, Feb. 15, 2010, pp. 3458-3476.
International Search Report and Written Opinion for PCT Patent Application No. PCT/EP2014/051918, dated Apr. 4, 2014, 14 pages.
International Preliminary Report on Patentability for PCT Patent Application No. PCT/EP2014/051918, dated Aug. 13, 2015, 11 pages.
Non Final Office Action for U.S. Appl. No. 14/758,792, dated Jan. 19, 2017, 6 pages.
Notice of Allowance for U.S. Appl. No. 14/758,792, dated May 19, 2017, 7 pages.

(56) References Cited

OTHER PUBLICATIONS

Notice of Allowance for U.S. Appl. No. 14/164,955, dated Sep. 30, 2015, 10 pages.
Office Action for Japanese Patent Application No. 2015-555722, dated Dec. 19, 2017, 7 pages (3 pages of English Translation and 4 pages of Official Copy).

* cited by examiner

SYSTEMS AND METHODS FOR SUB-APERTURE BASED ABERRATION MEASUREMENT AND CORRECTION IN INTERFEROMETRIC IMAGING

PRIORITY

The present application is a continuation application of U.S. patent application Ser. No. 14/758,792, filed Jun. 30, 2015, which is a National Stage of PCT/EP2014/051918, filed Jan. 31, 2014, which in turn claims priority to U.S. Provisional Application Ser. No. 61/759,854, filed Feb. 1, 2013 and U.S. Provisional Application Ser. No. 61/777,090 filed Mar. 12, 2013, the contents of which are hereby incorporated by reference.

TECHNICAL FIELD

The present application relates to optical imaging systems and methods, and in particular wavefront aberration detection and correction in interferometric imaging.

BACKGROUND

In an imaging system, an optical aberration occurs when light from one point of an object does not converge into a single point after transmission through the system. Optical aberrations can be described by the distortion of the wavefront at the exit pupil of the system. Ideally, light converging to a point should have a spherical wavefront. The wavefront is a locus of points with similar electromagnetic phase. The local direction of energy propagation is normal to the surface of the wavefront. FIG. 1 is a schematic showing an aberrated wavefront relative to an ideal reference wavefront. The exit pupil is the image of the aperture stop from the point of view of the image point. The direction of energy propagation can be described as a ray normal to the local wavefront. The deviation of the aberrated ray relative to an unaberrated ray at the image plane intersection describes the lateral error of the aberrated ray, which is usually associated with blurring and loss of information. As shown in FIG. 1, an aberrated wavefront lags/leads the ideal reference wavefront at different locations across its surface. The amount of this lead or lag is the local phase error. One can also see that the local slope, or tilt of the aberrated wavefront does not match that of the reference wavefront. Because the local direction of energy propagation is normal to the wavefront, this corresponds to rays propagating through the system with non-ideal paths. These aberrated rays are not perfectly coincident at the image plane, causing blurring and a loss of point-to-point image fidelity. Defocus is a special case of aberration, where the radius of curvature of the wavefront is such that the aberrated rays may converge to a point, albeit away from the desired image plane.

In the classic microscope, points in an object plane correspond to points in a detection plane, often sensed by an array detector. The above description of aberration in an imaging system clearly shows how light emanating from a particular object point might be distributed in the lateral direction, in the case of aberration over a number of neighboring pixels in the image sensor. In a coherence microscope, a reference reflection causes the information recorded at the sensor to encode information about the phase of the incident light relative to the reference reflection. When a broad bandwidth of light is used to illuminate the coherence microscope, this enables processing which can extract the optical path length between scattering objects and the reference reflection. Scattered light from objects at a particular optical pathlength or axial depth can be isolated from light scattered from any other depth. If each pixel of the image sensor is considered independently, a 3D volume can be constructed. In general the aberrated rays, misplaced on the sensor, distract from the useful information.

Recently it has been shown that the phase information in the original detected data set can be mathematically manipulated to correct for known aberrations in an optical coherence tomography volume[15] and the closely related holoscopy [18,22]. Methods have been described which attempt to iteratively solve for unknown aberrations, but these methods have been very limited in the precision of the corrected aberration, and are hindered by long execution times for the iterative calculations.

The use of Shack-Hartmann sensor based adaptive optics for wavefront aberration correction is well established in astronomy and microscopy for point like objects to achieve diffraction limited imaging [1-3]. It is currently an active field of research in optical coherence tomography/microscopy (OCT/OCM) [24,25]. Denk et al describe a coherence gated wavefront sensor where the object is illuminated with a single point of focused low coherence light to create an artificial 'guide star' and the focusing of the Shack-Hartmann sensor is realized either through a physical lenslet array or by computational method; where the low coherence property of the light allows depth selection in the wavefront measurement (see for example EP Patent No. 1626257 Denk et al. "Method and device for wave-front sensing"). Recently, adaptive optics via pupil segmentation using a spatial light modulator (SIM) was demonstrated in two photon microscopy [5]. The results showed that the sample introduced optical aberrations, due to change in the refractive index with depth in the sample, can be reduced to recover diffraction limited resolution. This can improve the depth of imaging in tissues. Such segmented pupil approach has also been shown with scene based adaptive optics [6]. Recently, Tippie and Fienup demonstrated sub-aperture correlation based phase correction as a post processing technique in the case of synthetic aperture digital off axis holographic imaging of an extended object [7]. This method allows for correction of narrow band interferometric data in a sample in which scatter or reflection from multiple depths can be ignored. If scatter from multiple depths are present, they may confuse the algorithm, or the algorithm may try to find some best fit to the various wavefront shapes presented to it arising from the variable defocus presented from the scatterers at different depths.

The key to the above recent advancements lies in the availability of phase information in the interferometric data. This information has been successfully exploited for implementing digital refocusing techniques in OCT, by measuring the full complex field backscattered from the sample. Current methods rely however on two assumptions: first, that the samples exhibit an isotropic and homogenous structure with respect to its optical properties, and secondly, that the aberrations, if present, are well defined, or accessible. Whereas the first limitation has not been addressed so far, the second issue can be solved either by assuming simple defocus and applying spherical wavefront corrections, or by iteratively optimizing the complex wavefront with a merit function that uses the image sharpness as a metric [14,15].

SUMMARY

Systems and methods for sub-aperture correlation based wavefront characterization and image correction as a post processing technique for broad bandwidth interferometric imaging to achieve near diffraction limited resolution in the presence of various order aberrations are described. In a most basic sense, the method involves isolating an axial subset of the interferometric data corresponding to a depth in the sample where a lateral structure is located, dividing the axial subset into lateral subsections at a plane where the wavefront should be characterized, determining a correspondence between at least two of the lateral subsections, characterizing the wavefront using the correspondence, and storing or displaying the wavefront characterization or using the wavefront characterization as input to a subsequent process. This method has the advantage of directly providing the local wavefront gradient for each sub-aperture in a single step. As such it operates as a digital equivalent to a Shack-Hartmann sensor. By isolating a particular axial depth in the image, for example according to the coherence length of the broad bandwidth source, the method can ignore scatter arising from other depths. This method can correct for the wavefront aberration at an arbitrary plane without the need of any adaptive optics, SLM, or additional cameras. The axial subset can be propagated to a plane where the characterization is to occur prior to the dividing into subsections. Theory, simulation and experimental results will be presented for the case of full field interference microscopy. The concept can be applied to any coherent interferometric imaging technique and does not require knowledge of any system parameters and furthermore does not rely on the assumption of sample homogeneity with respect to its refractive index. A swept-source optical coherence tomography (SS-OCT) system is one type of interference microscopic system for which the method could be applied. In one embodiment, a fast and simple way to correct for defocus aberration is described using only two sub-apertures or subsection correspondences. The aberration present in the images can be corrected without knowing the system details provided the image is band limited and not severely aliased. The method works very well when the spatial frequency content is spread uniformly across the pupil which is the case when imaging diffuse scattering object with laser light.

In a preferred embodiment, data from an optical coherence tomography (OCT) volume is used to calculate the aberrations present at a particular depth in the volume. From this knowledge the focus and higher order aberrations may be corrected, without prior knowledge of the system arrangement. Local correction and correction of aberrations induced throughout the sample may also be possible. Embodiments involving overlapping and non-overlapping sub-apertures are considered. The overlapping aperture method is believed to be novel to holography as well as OCT. The wavefront characterization can be used to correct the OCT image data and generate an image with reduced aberrations. In addition the wavefront characterization could have many uses including but not limited to being used as input to a wavefront compensation device, to a manufacturing process, or to a surgical process.

The systems and methods of the present application allow a deterministic approach to phase correction in OCT volumes. Prior methods to correct phase in OCT volumes depended on in depth, accurate knowledge of the system parameters and aberration, or an iterative approach to try out aberration corrections and select the one producing the best result. This method does not require long iterations as in case of optimization methods used for phase correction [14-16] and provides the phase error estimation in a single step. Phase correction in OCT volumes promises to remove the current tradeoff between sample lateral resolution and depth of focus, as well as ultimately remove the limitation on lateral resolution introduced by high order aberrations of the eye. This computational method introduces no expensive deformable mirrors or complex sensing apparatus. This technology is likely part of the solution that allows OCT to achieve unprecedented lateral resolution, without adding significant instrument cost.

BRIEF DESCRIPTION OF THE FIGURES

FIG. 5(a) shows the normalized Power spectrum of a light source used in numerical simulations. FIG. 5(b) shows the spectral interferogram at one lateral pixel on the camera. FIG. 5(c) is the FFT of the interferogram (A-scan) in FIG. 5(b), illustrating how scatter may be isolated to a particular depth according to the coherence length of the broad bandwidth source. FIG. 5(d) shows the image slice corresponding to the peak in FIG. 5(c) without any phase error. FIG. 5(e) shows the phase error in radians. FIG. 5(f) is the corresponding image obtained.

FIGS. 7(a), 7(b), 7(c) and 7(g) show the phase corrected images resulting from non-overlapping sub-aperture correction with values of K equal to 3, 5, 7, and 9 respectively, and FIGS. 7(d), 7(e), 7(f) and 7(j) are the residual phase error in radians corresponding respectively to FIGS. 7(a), 7(b), 7(c) and 7(g). FIGS. 7(h) and 7(i) are the images for sub-apertures with 50 percent overlap for K equal to 3 and 5, and FIGS. 7(k) and 7(l) are the respective residual phase error in radians.

FIG. 10(b) shows the quadratic phase error across the aperture in radians, FIG. 8(d) shows the estimated phase error in radians, and FIG. 10(e) shows the residual phase error in radians.

FIG. 12(a) shows the result obtained using non-overlapping sub-aperture with K=3. FIG. 12(b) shows the corrected image obtained with overlapping sub-apertures with K=3 with 50% overlap. FIG. 12(c) shows the corrected image for non-overlapping sub-apertures with K=5. FIGS. 12(d), 12(e) and 12(f) are the detected phase errors across the apertures in radians in the case of FIGS. 12(a), 12(b) and 12(c) respectively.

FIG. 13(a) shows the aberrated image of a USAF target with a uniform plastic sheet. FIG. 13(b) shows the phase corrected result using non-overlapping sub-aperture with K=3. FIG. 13(d) illustrates the corresponding phase error. FIG. 13(e) shows the defocus error resulting from the two non-overlapping sub-aperture processing technique shown in FIG. 9. FIG. 13(c) shows the image obtained with this phase error.

FIG. 14 (a) shows a tomogram of the grape sample with an arrow indicating a layer at the depth of 313.5 μm. FIG. 14 (b) shows an enface view of that layer and FIG. 14 (c) shows the defocus corrected image. FIG. 14(d) shows the corrected 3D volume of data.

DETAILED DESCRIPTION

Figure 2:
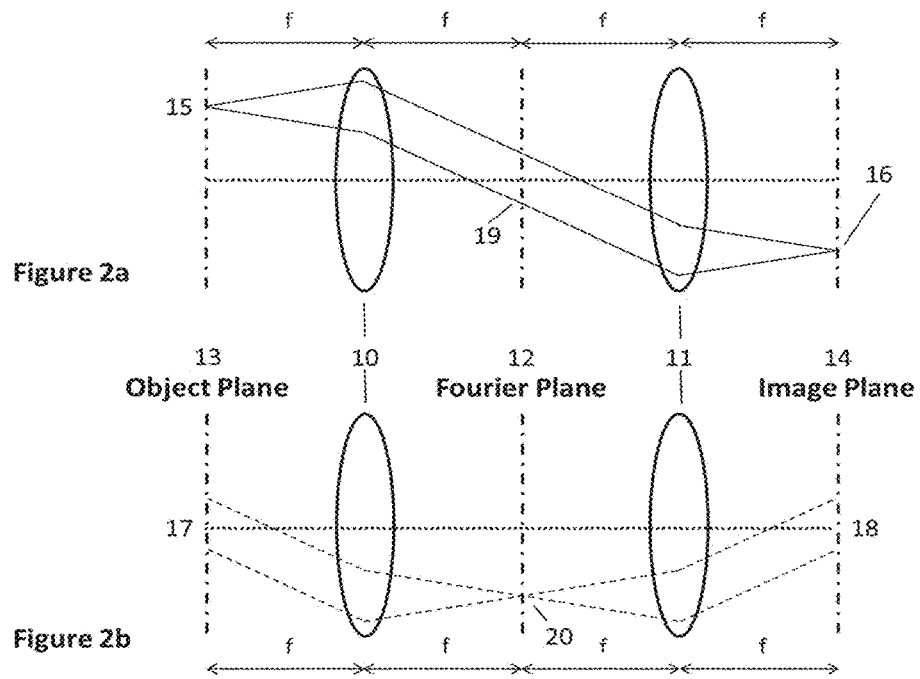
FIG. 2 illustrates background concepts of conjugate planes and Fourier planes useful for understanding aspects of the present application.

In the simplified optics described below, spaces are described with their imaging relationship to the object plane, which contains the object being investigated. Spaces within the system are identified as either optically conjugate to the object plane or at a Fourier plane with respect to the object plane. FIG. 2 is provided to illustrate these background concepts with a classic "4F" system. In the 4F system, a telescope is created with two lenses 10 and 11 each of focal length 'f'. A first, 'object', plane 13 is located one focal length in front of the first lens 10. An intermediate, 'Fourier', plane 12 is located at one focal length behind the first lens. The second lens 11 of focal length 'f' is placed a focal distance behind the intermediate plane. A third, 'image' plane 14 is located at one focal length behind the second lens. The first and the third planes 13 and 14 are 'optically conjugate'; there is a point to point correspondence of light in one plane to another as when traditionally imaged, as illustrated in FIG. 2a for points 15 and 16. Similarly, at optically conjugate planes there is a beam direction, to beam direction correspondence of light in one plane to another, as indicated in FIG. 2b for beams 17 and 18. At the intermediate 'Fourier' plane 12, light from a point in the object 15 corresponds to a collimated beam 19, or plane wave, and the angular orientation of the plane wave is determined by the position of the point in the object plane 13, as shown in FIG. 2a. Light from a collimated beam 17, or plane wave, in the object 13, corresponds to a point 20 in the Fourier plane 12; and the angular orientation of the plane wave in the object 13 is described by the position of the point in the Fourier plane 12, as shown in FIG. 2b.

The combination of plane waves at different incident angles results in sinusoidal interference which is well described by the spatial frequency of interference. We therefore describe different locations within a Fourier plane as containing the information about different spatial frequencies of the object plane. Pupil plane and 'far field' are used synonymously with a plane that is located at a Fourier plane relative to the object plane. Planes located between the object and Fourier plane, or between the Fourier and image plane can be described as defocused, but not entirely into the far field. Note that although the diagram illustrates point like imaging, real optical systems, have a limited spot dimension at an image plane. The full aperture of the optical system supports the transfer of plane waves from many directions. The sum of these plane waves can describe an arbitrary distribution of light. Further description of this formalism can be found in the book Linear Systems, Fourier Transforms, and Optics by Jack Gaskill hereby incorporated by reference.

Theoretical Formulation

Figure 3:
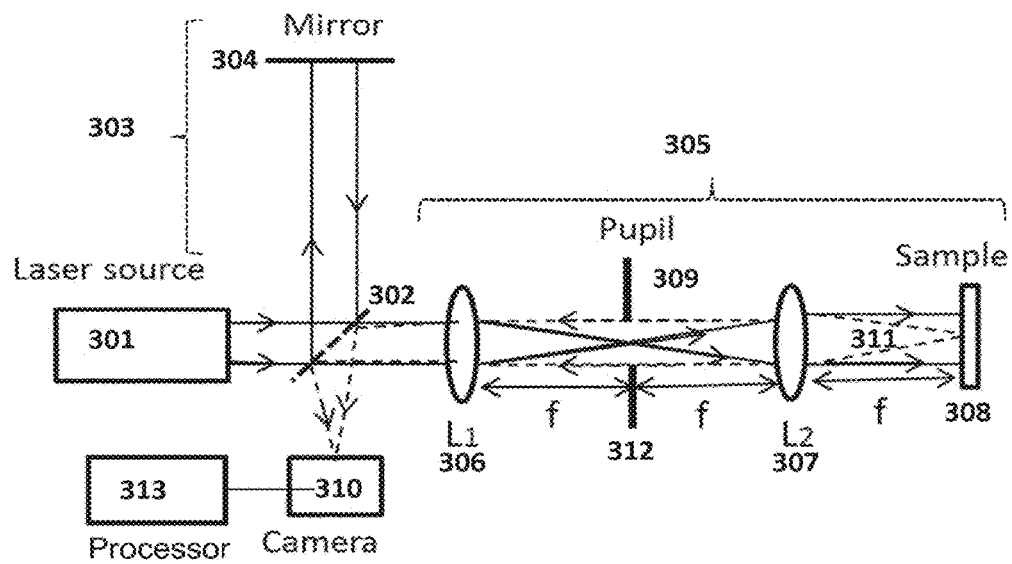
FIG. 3 illustrates a generalized interferometric imaging system capable of performing the method of the present application.

For a theoretical analysis of the method of the present application, a system based on a Michelson interferometer as shown in FIG. 3, is considered. The theory presented here is valid for any interferometric based system. For the system illustrated in FIG. 3, light from a laser source 301 passes through a beam splitter 302 where it is split into two paths. While a laser is indicated in the figure, any broadband light source could be used including frequency swept sources. The light in one arm, the reference arm 303, is reflected off a mirror 304 and directed back to the beam splitter. Light in the second path, the sample arm 305 passes through lenses L1 306 and L2 307 which form a 4F telecentric imaging system. After passing through the lenses, the light is directed towards an object to be imaged (sample) 308. The method could be applied to a variety of samples including but not limited to biological tissue, animal or vegetable products, gemstones, pearls, manufactured material process inspection (e.g. paint coatings, photovoltaic cells, plastic packaging). The sample should have structural content extending in the lateral direction. In particular, this method provides advantage when the sample is thick and presents reflections or scatter back to the detector from multiple depths.

The human eye provides a meaningful case where the retina provides a scattering volume with multiple layers observable by OCT. Within that scattering volume, structures or non-uniformities exist which may serve as landmarks for a correlation or registration operation. The anterior media and optics of the eye introduce phase distortions to light passing in and out of the eye. It is primarily these distortions that can be well corrected by applying phase corrections at a Fourier plane relative to the sample. Phase distortions introduced by the structures within the volume of the retina itself, such as can reasonably be expected by structures such as blood vessels, will have relatively more local phase distortions with a small isoplanatic patch size.

Light reflected from the sample is recombined with the reference light at beam splitter 302 and is directed towards a detector, in this case a 2D camera 310 with a plurality of pixels. The detector generates signals in response thereto. Dotted rays 311 show the imaging path of a point on the object in focus. The camera is at the focal plane of lens L1 306. A pupil aperture 309 can be placed at the Fourier plane 312 located at the focal length of the two lenses to limit the optical spatial frequency bandwidth to be less than the Nyquist limit of detection. If no limiting physical aperture is present at a Fourier plane, the other apertures of the system will have a defocused footprint at the Fourier plane. The sum of these aperture footprints will ultimately provide a bandwidth limit, albeit with some softness to the bandwidth edge, and typically some variation with field angle (vignetting). For these reasons it is advantageous that the pupil of the system be located at approximately a location corresponding to Fourier planes corresponding to the depths of the scattering object.

In this embodiment, light is incident upon a broad area of the sample to be imaged in a full field or wide field imaging technique and is collected all at once on the detector creating a three dimensional (3D) image volume. As will be described in further detail below, the inventive method could be applied to other interferometric imaging systems including scanning techniques like flying spot and line-field OCT that can create two-dimensional or three-dimensional data sets. The output from the detector is supplied to a processor 313 that is operably connected to the camera for storing and/or analysis of the detected signals or data. A display (not shown) could be connected for display of the data or the resulting analysis. The processing and storing functions may be localized within the interferometric data collection instrument or functions may be performed on an external processing unit to which the collected data is transferred. This unit could be dedicated to data processing or perform other tasks which are quite general and not dedicated to the interferometric imaging device.

The interference causes the intensity of the interfered light to vary across the optical frequency spectrum. The Fourier transform of the interference light across the spectrum reveals the profile of scattering intensities at different path lengths, and therefore scattering as a function of depth in the sample. The interference of the light reflected from the object and reference mirror is adequately sampled in a lateral direction using a 2D camera placed at the image plane of the object. For simplicity, a 4F telecentric imaging system is assumed, and the object field is band limited by a square aperture at the pupil plane. In 2D interferometric imaging, the recorded intensity signal on the detector $I_d$ at point $\xi$ in the detection plane, at the optical frequency k of the laser is given by:

$$I_d(\xi;k)=|E_s(\xi;k)|^2+|E_r(\xi;k)|^2+E_s^*(\xi;k)E_r(\xi;k)+E_s(\xi;k)E_r^*(\xi;k). \quad (1)$$

$E_s$ and $E_r$ are the electric fields at the detector from the object and the reference arm respectively expressed as:

$$E_s(\xi;k)=\exp(i4kf)E'_s(\xi;k)=\exp(i4kf)\int E_o(u;k)P(\xi-u;k)du^2 \quad (2)$$

and $$E_r(\xi;k)=R(\xi;k)\exp[ik(4f+\Delta z)/c] \quad (3)$$

where $E_o$ is the object field convolved with the three-dimensional point spread function (PSF) P of the system, u is a point in object plane, R is the local reference field amplitude, $\Delta z$ denotes the optical path length difference between the sample and the reference arms, and c is the velocity of light.

In the case of monochromatic illumination, with effectively single optical frequency, k, the complex signal $I_s=E_sE_r^*=E'_s R$ can be retrieved via phase shifting methods where $\Delta z$ is varied [8-9]. Phase shifting methods are also used to detect the complex wavefront employing broad band light sources which provide coherence gating [10]. The complex signal $I_s$ can also be detected via frequency diversity as in the case of swept source OCT. In this case, the object may be placed completely on one side of the reference mirror and the complete interference signal is recorded by varying optical frequency. The Fourier transformation along the optical frequency dimension yields the tomographic signal separated from autocorrelation, constant intensity offset (DC) and complex conjugate terms [11]. The location of a source of scatter can be isolated in depth to within the coherence length of the source as is well understood in OCT. This coherence gate limits the resolution to which a plane containing the lateral structures can be isolated with this method. It is assumed that the aberrations present in the system primarily originate from the sample and sample optics and can be represented by an effective phase error at the Fourier plane.

The complex signal, $I_s(\xi,z)$ obtained after k→z Fourier transformation, containing field information about structure in the object's $z^{th}$ layer can be written in the discrete from as:

$$I_s(\xi,z)=\Delta\xi^2(m\Delta\xi,n\Delta\xi)=I_{m,n} \quad (4)$$

where $\Delta\xi$ is the detector pixel pitch assumed to be same in both directions, in and n determine the pixel location. Let the size of the sample be A×M pixels. After embedding the 2D signal into an array of zeros twice its size (2M×2M), the 2D discrete Fourier transform (DFT) of the signal $I_s$ is calculated by the processor to propagate the signal to the Fourier plane; that is, to propagate the field information about the objects $z^{th}$ layer from the plane in the system where it was acquired, to a plane in the system where it is desirable to characterize the wavefront.

$$D_{x,y} = DFT[I_{m,n}] = \sum_{m=0}^{2M-1}\sum_{n=0}^{2M-1} I_{m,n}\exp\left[-i2\pi\left(\frac{mx}{2M}+\frac{ny}{2M}\right)\right] \quad (5)$$

Figure 4:
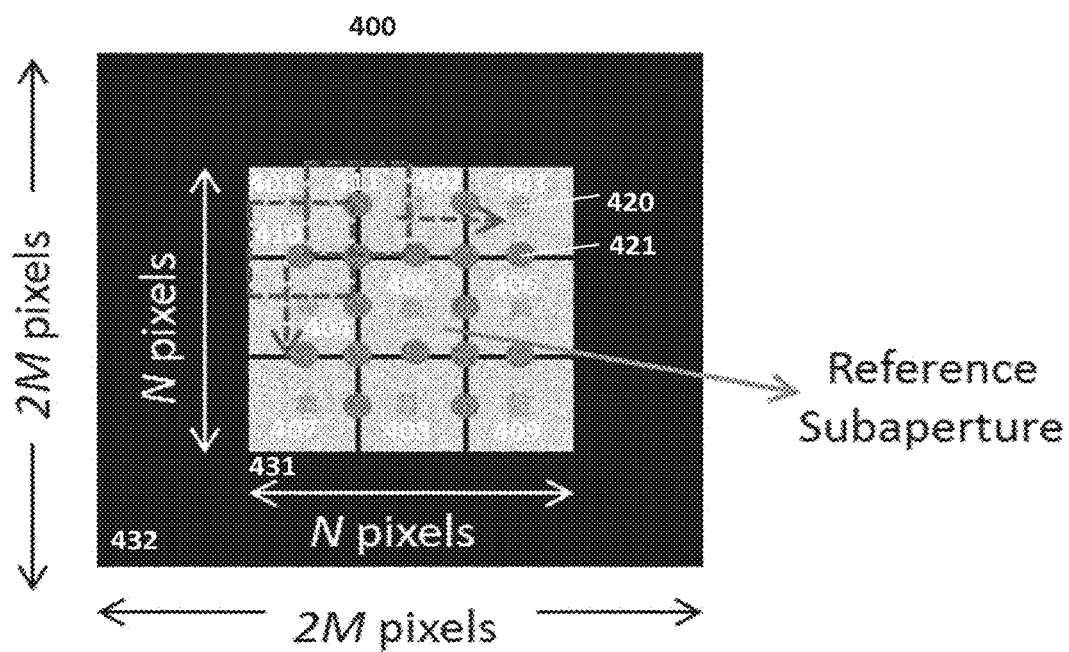
FIG. 4 illustrates how an image could be divided into different sub-apertures for determining aberrations according to the present application.

In Eq. (5), the constant complex factor due to propagation has been neglected as it does not affect the reconstruction of intensity images, which is of primary interest. The extent of the spatial frequency is limited due to the square pupil aperture. Let the extent of spatial frequencies in the Fourier plane be N×N pixels (2M>N), then according to the paraxial approximation:

$$L \approx N\Delta x = N\frac{\lambda f}{2M\Delta\xi} \quad (6)$$

where L is the length of the side of the square aperture, λ in is the central wavelength, f is the focal length of the lens and $\Delta x$ is the pixel pitch in the pupil plane. As is illustrated in FIG. 4, The N×N pixel data 431 is windowed out at the Fourier plane, embedded into the middle of array of zeros of size 2M×2M 432 and segmented into K×K sub-apertures with size $\lfloor N/K \rfloor \times \lfloor N/K \rfloor$ pixels, where $\lfloor . \rfloor$ is the floor function and K is usually odd so that the central sub-aperture can be selected as a reference. This figure shows the segmentation of Fourier data 400 into two different subsections or sub-aperture arrangements. The first arrangement, indicated by solid lines, is K×K non-overlapping sub-apertures with K=3. Each sub-aperture in this arrangement (401, 402, 403, 404, 405, 406, 407, 408, 409) would have N/3 pixels. The square dots 420 represent sampling points of the average local slope data due to non-overlapping sub-apertures. The dashed boxes 410 and 411 combined with the solid line boxes illustrate an overlapping sub-aperture arrangement with approximately 50% overlap in both directions. The circles 421 represent the sampling points of the overlapping apertures. With overlapping apertures, the number of sampling points is increased which reduces the error in phase estimation. The terms split aperture or partial aperture could be used analogously to sub-aperture in describing the general approach. While square apertures are used throughout the description, any shaped aperture or subsection which allows for mathematical transformation could be used.

Let $\tilde{D}_p$ and $\tilde{D}_q$ represent any two square sub-apertures of the filtered and segmented pupil data, $\tilde{D}$, given by $$\tilde{D}_p = \tilde{S}_p \exp(i\phi_p) \approx \tilde{S}_p \exp\left\{i\left[\phi_{po} + (x-x_{po})\frac{\partial\phi_p}{\partial x} + (y-y_{po})\frac{\partial\phi_p}{\partial y}\right]\right\} \quad (7)$$

$$\tilde{D}_q = \tilde{S}_q \exp(i\phi_q) \approx \tilde{S}_q \exp\left\{i\left[\phi_{qo} + (x-x_{qo})\frac{\partial\phi_q}{\partial x} + (y-y_{qo})\frac{\partial\phi_q}{\partial y}\right]\right\} \quad (8)$$

where $\tilde{S}_p$ and $\tilde{S}_q$ represent ideal aberration free data with $\phi_p$ and $\phi_q$ phase error, $$\left(\frac{\partial\phi_p}{\partial x}, \frac{\partial\phi_p}{\partial y}\right) \text{ and } \left(\frac{\partial\phi_q}{\partial x}, \frac{\partial\phi_q}{\partial y}\right)$$

are the average slope, $(x_{po}, y_{po})$ and $(x_{qo}, y_{qo})$ are the center pixels respectively in the $p^{th}$ and $q^{th}$ sub-aperture. It is assumed that any given sub-aperture is small enough such that the phase error can be approximated by the first order Taylor series. The 2D inverse discrete Fourier transform (IDFT) of $\tilde{D}_p$ and $\tilde{D}_q$ can be calculated to propagate back to the image plane according to:

$$IDFT[\tilde{D}_p] = \frac{1}{4M^2}\sum_{x=0}^{2M-1}\sum_{y=0}^{2M-1}\tilde{S}_{p_{x,y}}\exp(i\phi_p)\exp\left[i2\pi\left(\frac{mx}{2M} + \frac{ny}{2M}\right)\right] \approx \quad (9)$$

$$I_p\left(m - \frac{M\partial\phi_p}{\pi\partial x}, n - \frac{M\partial\phi_p}{\pi\partial y}\right)$$

$$IDFT[\tilde{D}_q] = \frac{1}{4M^2}\sum_{x=0}^{2M-1}\sum_{y=0}^{2M-1}\tilde{S}_{q_{x,y}}\exp(i\phi_q)\exp\left[i2\pi\left(\frac{mx}{2M} + \frac{ny}{2M}\right)\right] \approx \quad (10)$$

$$I_q\left(m - \frac{M\partial\phi_q}{\pi\partial x}, n - \frac{M\partial\phi_q}{\pi\partial y}\right).$$

$I_p$ and $I_q$ are the low resolution image version of $I_s$ and it is assumed that both have the same intensity, thereby correlating versions of the structure contained in the at least two subsections. The intensities of $I_p$ and $I_q$ are cross correlated to determine a correspondence such as the relative shift or translation between the two, from which the relative local wavefront slope in each sub-aperture can be expressed as:

$$s_{x_{po,qo}} = \frac{\partial\phi_p}{\partial x} - \frac{\partial\phi_q}{\partial x} = \frac{\Delta m\pi}{M}; \quad (11)$$

$$s_{y_{po,qo}} = \frac{\partial\phi_p}{\partial y} - \frac{\partial\phi_q}{\partial y} = \frac{\Delta n\pi}{M}, \quad (12)$$

where $\Delta m$ and $\Delta n$ are the shift in terms of pixels in x and y direction, po, qo are the center points in the $p^{th}$ and $q^{th}$ sub-aperture to which local slope data value is assigned. This is an interesting result as the slope data obtained is independent of any system parameters. The central sub-aperture is selected as the reference and the relative slope of the wavefront is calculated in other sub-apertures and the corresponding slope values are assigned to the center pixel in each sub-aperture.

The slope information is used to reconstruct the estimated wavefront error over the full aperture, $\phi_e$, can be modeled as a linear combination of Taylor monomials, $T_J$, according to:

$$\phi_e = \sum_{J=1}^{Z} T_J(X,Y) = \sum_{J=2}^{Z}\sum_{j=0}^{J} a_{Jj} X^j Y^{J-j}, \quad (13)$$

$$X = x - M \quad \ldots \quad 0 \le x \le 2M-1 \quad (14)$$
$$Y = y - M \quad \ldots \quad 0 \le y \le 2M-1$$

where X and Y represent the pixel location in Cartesian coordinate with the center pixel in the whole data array as the origin, Z is the highest order of the monomials and $a_J$ are the coefficients desired to determine. Constant and linear terms in $\phi_e$ are neglected as they do not cause the blurring of the image. The gradient of the phase error is then given by $$\nabla\phi_e = \sum_{J=2}^{Z}\sum_{j=0}^{J} a_{Jj}\nabla(X^j Y^{J-j}). \quad (15)$$

By comparing the slope data $S = (s_{x,1} \ldots s_{x,Ns}, s_{y,1} \ldots s_{y,Ns})^T$ with the gradient of the phase error $$G = \left(\frac{\partial\phi_e}{\partial x}\bigg|_1 \ldots \frac{\partial\phi_e}{\partial x}\bigg|_{Ng}, \frac{\partial\phi_e}{\partial y}\bigg|_1 \ldots \frac{\partial\phi_e}{\partial y}\bigg|_{Ng}\right)^T$$

in Eq. (15) at the locations of the central pixels in each sub-aperture, a solution in the form of the matrix is determined according to:

$$GA = S \quad (16)$$

where $A = (a_{20} \ldots a_{ZZ})$ is the coefficient matrix which to be determined, $N_s = K \times K$ is the number of sub-apertures and $N_g = \{[Z(Z+1)/2] - 3\} \le N_s$. The least square solution to Eq. (16) is found as:

$$A = (G^T G)^{-1} G^T S. \quad (17)$$

Taylor monomials are used as they are simple to use. Zernike polynomials can be also be used, but one has to take care that they are orthogonal over the sampled aperture and the solutions are different for apertures of different shapes [12]. Similarly the gradient is used as a description of the local surface orientation, however the surface normal vector would provide similar information. The simulations show that Taylor monomials work well enough in the determination of the phase error. In general, any holistic description of a surface that can be composed from a combination of local surface orientations, that can be individually determined by image correlation are applicable to this purpose.

Once the coefficients and the phase error $\phi_e$ have been estimated, the phase correction, $\exp(-i\phi_e)$ is applied to the Fourier data $\tilde{D}$ and then the 2D IDFT is performed to get the phase corrected image $\tilde{I}_s$ given by:

$$\tilde{I}_s = \frac{1}{4M^2}\sum_{x=0}^{2M-1}\sum_{y=0}^{2M-1}\tilde{D}_{x,y}\exp(-i\phi_e)\exp\left[i2\pi\left(\frac{mx}{2M} + \frac{ny}{2M}\right)\right]. \quad (18)$$

Note that $\tilde{D}$ is zero outside the bounds of the pupil defined by N×N pixels. This process can be repeated for all the layers suffering from aberration in case of a 3D volume image to get an aberration free volume image. A 4F system is assumed with the pupil and the Fourier plane being the same. As it has been shown that the method is independent of any system parameters, it can be applied to the Fourier transform of the image even if the pupil is not at the Fourier plane. One should, however, take care that the data is sampled at sufficient density to satisfy the Nyquist criteria for the optical spatial frequency band limit of the system. Otherwise, aliasing of higher spatial frequencies might disturb proper reconstruction when performing 2-D DFT on the image.

Computer Simulation

The theoretical construct was demonstrated using computer simulation. An aberrated data set is first simulated by calculating a predetermined offset from a relatively unaberrated acquisition from a real optical system. Using this simulated data set, aspects of the current method are applied.

Figure 5:
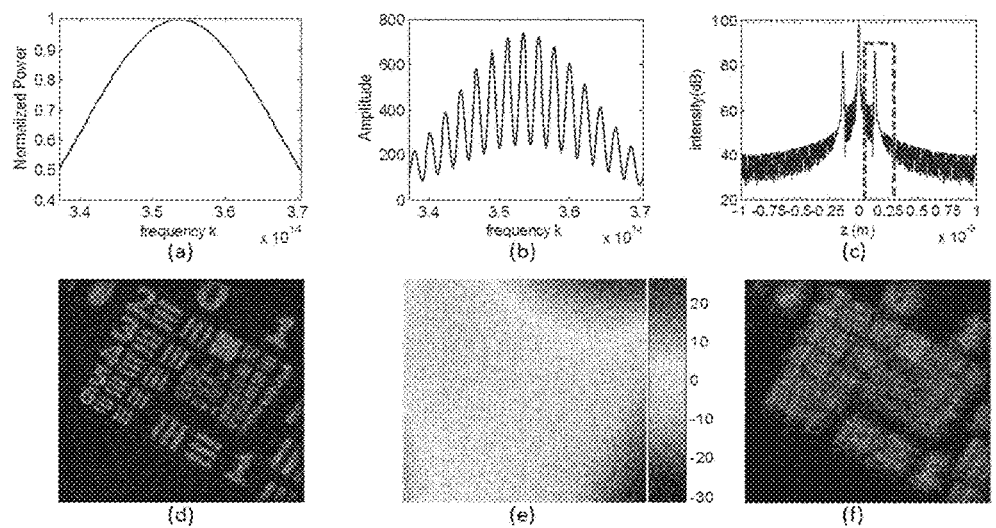
FIG. 5 displays data at various stages of the sub-aperture based detection and correction technique of the present application.

The computer simulation is based on the same optical setup shown in FIG. 3 with the focal length of lenses L1 and L2 as f=50 mm. A sweeping laser source with center wavelength $\lambda_0$=850 nm and bandwidth $\Delta\lambda$=80 nm is used for the simulation but any broad bandwidth source could be used. FIG. 5(a) shows the normalized power spectrum with respect to frequency $k=c/\lambda$. It is assumed that the sweeping is linear in optical frequency. For simplicity, just for the demonstration of the working principle of the method, only a 2D object which gives diffuse reflection on illumination is considered. The object being simulated is a USAF bar target of size 512×512 pixels, multiplied with circular complex Gaussian random numbers to simulate speckle noise.

First, the aberrated object measurement is simulated from a relatively unaberrated, real measurement. The measured object image, in this case a horizontal "slice" of data, is zero-padded to the size of 1024×1024 pixels and a fast Fourier transform (FFT) is performed to calculate the field present at the pupil plane where the wavefront is to be characterized. The result is multiplied with a square aperture which is an array of unity value of size of 512×512 pixels zero padded to size 1024×1024 pixels. To apply a phase error the result is multiplied with a factor $\exp(i\phi_e)$ given in Eq. (13) and then the inverse fast Fourier transform (IFFT) is computed to propagate the field back to the image plane. In the last step, the IFFT is computed instead of an FFT simply to avoid inverted images without actually effecting the phase correction method. The resulting field at the image plane is multiplied with a phase factor of $\exp(i2kf/c)$ to take into account the additional propagation distance, the delayed reference on-axis plane wave with phase factor of $\exp\{i2k(f+\Delta z)/c\}$ with $\Delta z$=60 μm is then added, and the squared modulus is finally calculated to obtain the simulated interference signal as would be measured at the detector. This is done for each optical frequency in the sweep to create a stack of 2D interference signals with optical frequency varying from $3.3708\times10^{14}$ sec$^{-1}$ to $3.7037\times10^{14}$ sec$^{-1}$ in 256 equal steps. The reference wave intensity was 100 times the object field intensity.

Aspects of the present application can then be applied to the simulated interferometric imaging data. First, an OCT volume is calculated from the simulated data without phase corrections by transforming along the optical frequency axis. The FFT of the 256 spectral pixels after zero padding to size 512 pixels is calculated for each lateral pixel of the detection plane (1024×1024 pixels) allowing one to separate the DC, autocorrelation and the complex conjugate term from the desired object term, in the axial direction. The desired object term is an axial subset of the full volume data set that is relatively free of confusing factors.

FIG. 5(b) shows the spectral interferogram at one lateral pixel on the camera; FIG. 5(c) is the FFT of the interferogram (A-scan) in FIG. 5(b); and FIG. 5(d) shows the isolated image slice from the reconstructed image volume at the position of the peak contained in the dashed rectangular box in FIG. 5(c) without any phase error. The simulated phase error consisted of Taylor monomials up to 6$^{th}$ order and the coefficients were selected from the random Gaussian distribution such that the peak to valley phase error across the aperture is 58.03 radians. FIG. 5(e) shows the simulated phase error in radians and FIG. 5(f) is a corresponding isolated aberrated image plane obtained after applying the phase error shown in FIG. 5(e). It is assumed that the phase error is independent of the optical frequency and that the system is compensated for any dispersion effects.

Figure 6:
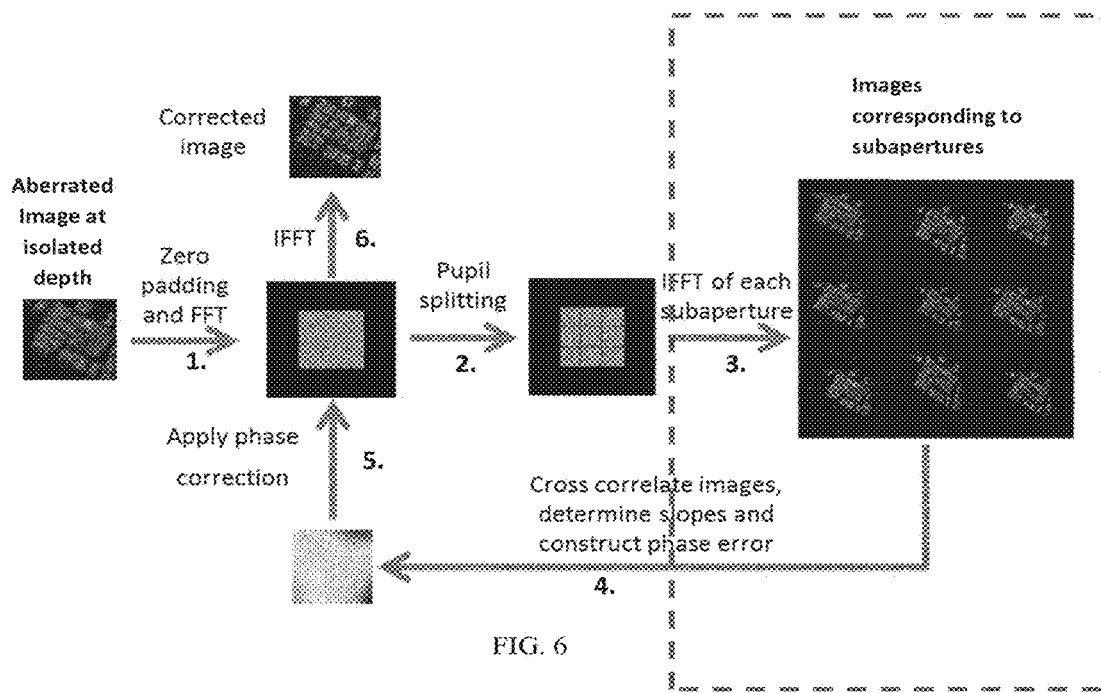
FIG. 6 illustrates the general steps involved with the sub-aperture based measurement and correction technique of the present application.

FIG. 6 shows a schematic diagram for the generalized estimation and correction of phase error based on a preferred embodiment of the inventive method. In the first step, the isolated aberrated image in FIG. 5(f) of size 512×512 pixels is zero-padded to size 1024×1024 pixels and the FFT is computed to propagate to the plane where the wavefront is to be characterized, in this case, the Fourier plane. This propagation step is optional depending on the desired plane to be characterized and data acquisition parameters. In the second step, the aperture, which in this simulation is a square of size 512×512 pixels, is split into K×K subsections or sub-apertures where K is an odd number. In the third step, the IFFT of two or more sub-apertures are computed. In the fourth step, an image from the central sub-aperture is selected as a reference and this reference is cross correlated with the other images using an efficient subpixel registration technique [13] to obtain correspondences between the subsections. The slopes and phase error can be calculated using the correspondences according to Eq. 11 to 17, thereby generating a wavefront characterization. In the fifth step, the phase correction is applied to the full aperture in the Fourier plane and finally in the sixth step, the IFFT is computed to get the phase corrected image as in Eq. (18).

Figure 7:
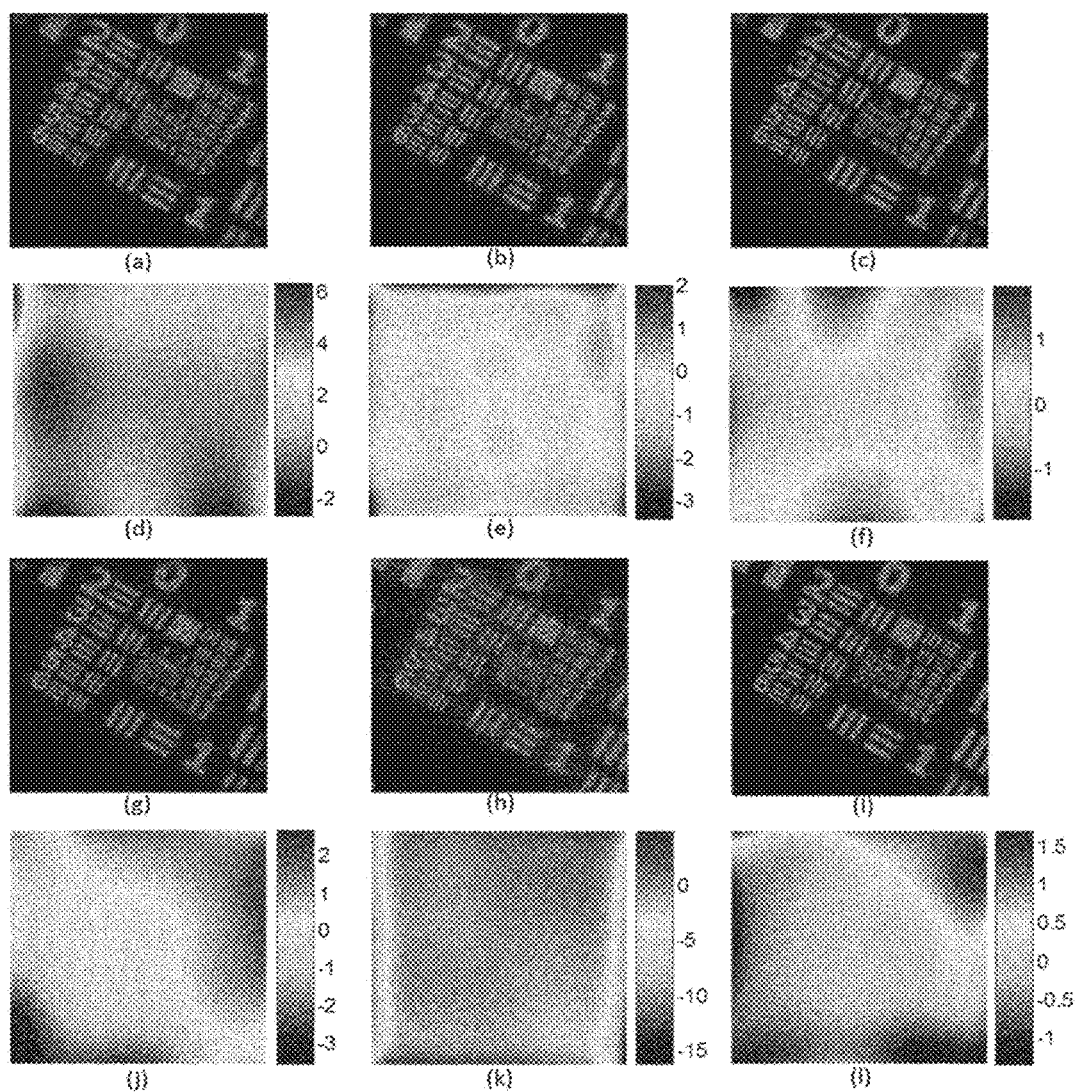
FIG. 7 illustrates corrected images resulting from various sub-aperture configurations.

FIG. 7 compares the corrected images resulting from various sub-aperture configurations. FIGS. 7(a), 7(b), 7(c) and 7(g) show the phase corrected images resulting from non-overlapping sub-aperture correction with values of K equal to 3, 5, 7, and 9 respectively, and FIGS. 7(d), 7(e), 7(f) and 7(j) are the residual phase error in radians corresponding respectively to FIGS. 7(a), 7(b), 7(c) and 7(g). FIGS. 7(h) and 7(i) are the images for sub-apertures with 50 percent overlap for K equal to 3 and 5, and FIGS. 7(k) and 7(l) are the respective residual phase error in radians.

In FIG. 7(a) K=3 and there are 9 sampling points which were fit using only the first 9 Taylor monomials according to Eq. (13). But, comparing to the degraded image in FIG. 5(f) to the image in FIG. 7(a) it is evident that the image quality has improved. In FIG. 7(b) with K=5, there are 25 sampling points which could be fit using Taylor monomials up to 6$^{th}$ order with 25 coefficients. The residual phase error has reduced for K=5 in FIG. 7(e) as compared to the K=3 case in FIG. 7(d). In FIGS. 7(c) and 7(g), K=7 and K=9 respectively, but only Taylor monomials up to 6$^{th}$ order were used to see the effect of increasing sampling points. The residual error decreases for K=7 but increases for K=9. This is because with increasing K size, the sub-apertures become smaller and hence resolution of the images corresponding to these sub-apertures also reduces leading to registration error for shift calculations. This results in error in slope calculation and phase error estimation. Obviously increasing the number of apertures allows in principle for higher order phase correction, but the smaller number of pixels in the sub-aperture leads to increasing phase errors.

Overlapping sub-apertures with fifty percent overlap were also tried in order to increase the sampling points with uniform spacing and to maintain the number of pixels of the sub-apertures. Fifty percent overlap ensures a maximum number of sampling points without the over redundancy of the sub-aperture data due to overlap. In case of overlapping apertures, K no longer stands for the number of sub-apertures but defines the size of the aperture as $\lfloor N/K \rfloor \times \lfloor N/K \rfloor$ pixels. For K=3 there is higher residual error as compared to the non-overlapping case and some aberration in the image in FIG. 7($h$) are also apparent. But, the residual error decreases for the overlapping case when K=5. This is because in case of K=3 the average slope for phase correction is calculated over a larger sub-aperture capturing more aberrations than the non-overlapping case. But, the residual error decreases rapidly for the overlapping case when K=5. In case of K=s the size is small enough to reduce this error and reduction in the residual phase error in FIG. 7($l$) is apparent. The optimum number of sub-apertures and degree of overlapping may change depending on the aberrations present and specifics of the data collection system.

Figure 8:
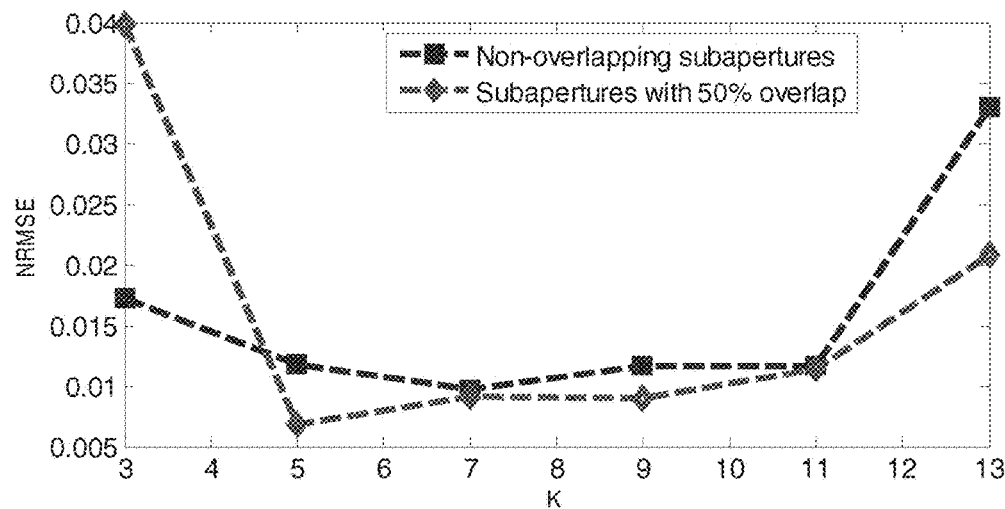
FIG. 8 shows a plot of normalized residual phase error for different values of K for both non-overlapping (square markers) and overlapping (circular markers) sub-apertures.

FIG. 8 shows a plot of normalized residual phase error (RMS error) for different values of K for both non-overlapping (square markers) and overlapping (diamond markers) sub-apertures for the specific optical data collection system described. With overlapping sub-apertures of appropriate size with respect to the overall aberrations we obtain in general a lower residual phase error. Smaller sized sub-apertures (K>11 in FIG. 8) lead to loss of resolution and increased registration error which leads to increase in residual phase error. For larger sub-apertures there is the problem of wavefronts sampled with less sampling points and hence only coefficients for the lower order Taylor monomials can be found. In addition, large apertures can lead to suboptimal results in the case of significant system aberrations.

Figure 9:
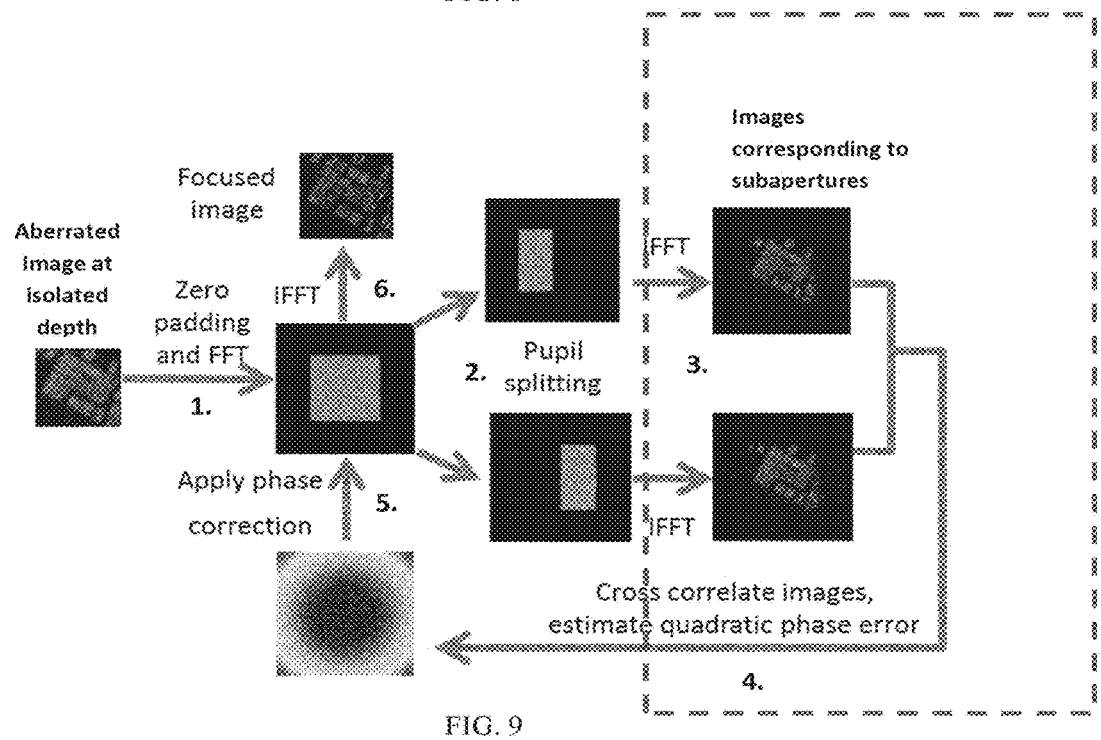
FIG. 9 illustrates the steps involved with a particular embodiment of the method of the present application directed towards correcting for defocus in which only two sub-apertures are used.
Figure 10:
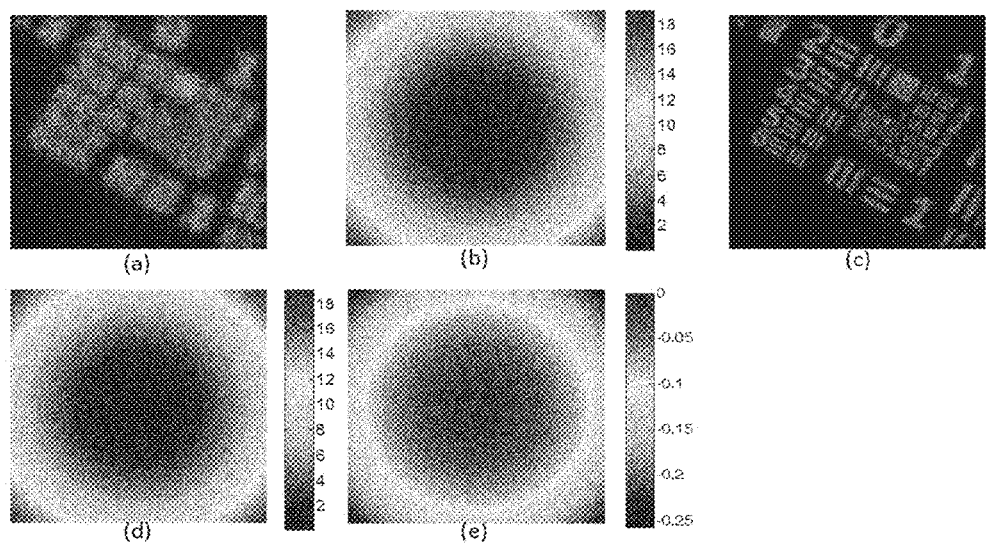
FIG. 10 shows the simulated defocused image (FIG. 10(a)) and the phase corrected image (FIG. 10(c)) using the two sub-aperture method for correcting for defocus.

In the case of symmetric quadratic phase error across the aperture which results in defocus aberration, it is possible to characterize the wavefront with just two sub-apertures. FIG. 9 shows the schematic for the steps involved with this embodiment. In the first step, the isolated aberrated image is zero padded and Fourier transformed to propagate to the plane where the wavefront is to be characterized, in this case the Fourier plane. In the second step, the resulting aperture can be split into two portions, preferably either vertically or horizontally. It is not necessary for the two portions to account for the entire aperture. In the third step, the IFFT of the two sub-apertures are computed. In the fourth step, images from the two sub-apertures are cross correlated with each other to obtain correspondences between the subsections and estimate the phase error. The phase error term in each half has a linear slope with equal magnitude but opposite direction. Using the relative shift information by cross correlating the images formed using two half apertures, one can easily derive the estimate of the coefficient of the quadratic phase as:

$$a = \frac{2\pi \Delta m}{MN} \quad (19)$$

where $\Delta m$ is the shift in terms of pixels in x direction, 2M is the total size of the data array in pixels and N is the size of the aperture in pixels. From Eq. (19) the quadratic phase error can be estimated. In the fifth step, the phase correction is applied to the full aperture in the Fourier plane and finally in the sixth step, the IFFT is computed to get the phase corrected or focused image. This method is simple and fast as compared to the defocus correction method based on sharpness optimization which requires long iterations. FIG. 10 shows the simulated defocused image (FIG. 10($a$)) and the phase corrected image (FIG. 10($c$)) using the two sub-aperture method for correcting for defocus. FIG. 10($b$) shows the quadratic phase error across the aperture in radians, FIG. 10($d$) shows the estimated phase error in radians, and FIG. 10($e$) shows the residual phase error in radians.

Experimental Verification

Figure 11:
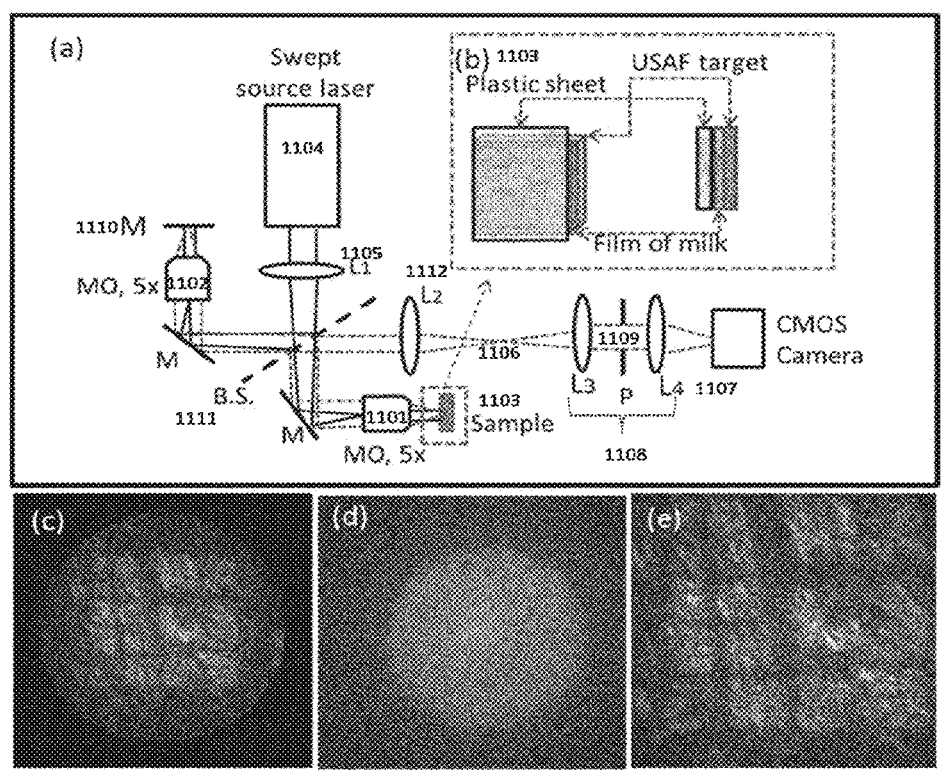
FIG. 11(a) is a schematic of the swept-source full-field optical coherence tomography (SSFF-OCT) setup for the experimental verification of the method of the present application.
FIG. 11(b) illustrates two views of the sample consisting of a layer of plastic, a film of dried milk and an USAF bar target.
FIG. 11(c) shows the image of the UASF bar target surface obtained with non-uniform plastic sheeting.
FIG. 11(d) shows the Fourier transform of the image, where the information content is limited to a central area corresponding to the spatial frequency band limit of the optical system.
FIG. 11(e) shows the zoomed in image of FIG. 11(c) showing 390×390 pixels.

The schematic of the full-field swept-source optical coherence tomography (FF SS-OCT) setup for the experimental verification of the present application is shown in FIG. 11($a$). The system is a simple Michelson interferometer based on a Linnik configuration with same type of microscope objectives (5× Mitotuyo Plan Apo NIR Infinity-Corrected Objective, NA=0.14, focal length f=40 mm) 1101 and 1102 in both the sample and reference arms. The sample 1103 illustrated in two different views in FIG. 1 ($b$) consists of a layer of plastic, a film of dried milk and an USAF resolution test target (RTT). The view on the left shows the sample in the x-y plan perpendicular to the beam propagation direction. The view on the right shows the 3 layers along the beam propagation direction or z-axis. A thin film of dried milk was used to produce scattering and diffuse reflection. The plastic layer of non-uniform thickness and structure to create random aberrations was created by heating a plastic used for compact disc (CD) cases. The output beam from the sweeping laser source 1104 (Superlum BroadSweeper 840-M) incident on the lens L1 1105 is of diameter 10 mm and the field of view on the sample is ~2 mm. The power incident on the sample is 5 mW. The RTT surface was in focus while imaging. The image 1106 of the sample formed by L2 1112 is transferred to the camera plane 1107 using a telescope 1108 formed by lenses L3 and L4 with effective magnification of 2.5×. A circular pupil P 1109 of diameter 4.8 mm is placed at the focal plane of lens L3 and L4 to spatially band limit the signal. M is the mirror 1110 in the reference arm, B.S. is the beam splitter 1111 that splits and combines the sample and reference arms, 1101 and 1102 are 5×NIR microscope objectives, L1 and L2 are lenses with focal lengths f=200 mm, L3 and L4 are lenses with f=150 mm and 75 mm and P is the pupil placed at the focal plane of L3 and L4.

FIG. 11($c$) shows the depth isolated image of the RTT surface obtained with non-uniform plastic sheeting. The image contains speckle due to scattering at the milk film and aberrations from the plastic layer. For imaging, the laser is swept from wavelength λ=831.4 nm to λ=873.6 nm with Δλ=0.0824 nm step width and the frames at each wavelength are acquired using a CMOS camera (Photon Focus MV1-D1312I-160-CL-12) at the frame rate of 108 frames per second synchronized with the laser. A total of 512 frames are acquired. The RTT surface is in focus while imaging. After zero padding and λ to k mapping of the spectral pixels, a 1-D FFT is performed along the $k^{th}$ dimension for each lateral pixel to provide depth information on different layers of the sample. FIG. 11($d$) shows the Fourier transform of the measured image. The zero values observed beyond the radius corresponding to the pupil are consistent with a signal that is band limited and sufficiently sampled, with some oversampling relative to the Nyquist limit. The depth layer corresponding to the RTT is selected for aberration correction. FIG. 11(e) shows the zoomed in image of FIG. 11(c) showing 390×390 pixels. It is barely possible to clearly resolve the RTT element (4, 3) in this image. The horizontals bars are visually more affected by the aberration due to the anisotropic nature of the distorted plastic layer. The FFT of the image shown in FIG. 11(d) after zero padding shows the spatial frequency information within a circular area. For further processing, a square area was filtered out with sides equal to the diameter of the circle, which was about 600 pixel units.

Figure 12:
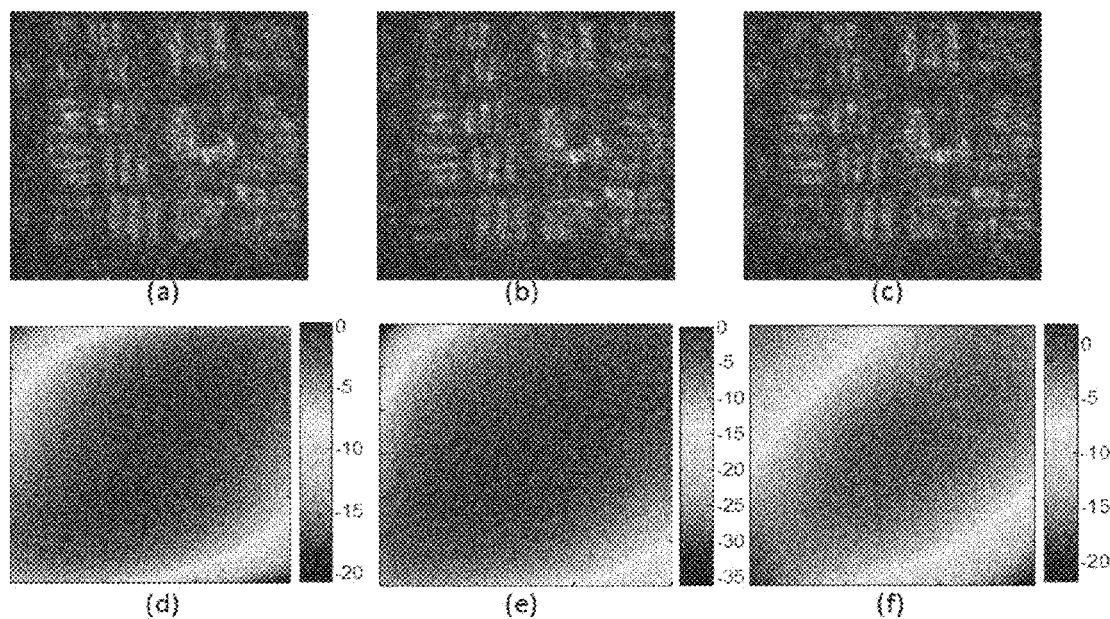
FIG. 12 shows the phase correction results after sub-aperture processing for several different sub-aperture configurations.

FIG. 12 shows the phase correction results after sub-aperture processing for several different sub-aperture configurations. Taylor monomials up to $5^{th}$ order are fitted to determine the phase error in this example. FIG. 12(a) shows the corrected image result obtained using 9 non-overlapping sub-apertures with K=3. In this case, fitting included only up to the first nine monomial terms given by Eq. (13) and hence monomial fitting limited to the $4^{th}$ order. FIG. 12(b) shows the corrected image obtained with overlapping sub-apertures with K=3 and 50% overlap. FIG. 12(c) shows the corrected image for non-overlapping sub-apertures with K=5. The images get a bit sharper. Horizontal bars up to (5, 1) in FIG. 12(a), (5, 2) in FIG. 12(b) and (5, 4) in FIG. 12(c) can be resolved. This corresponds to the improvement in resolution by a linear factor of 1.6, 1.8 and 2 for the case in FIGS. 10(a), 10(b) and 10(c) respectively. The improvement in resolution is calculated using the relation $2^{n+m/6}$ where n is the improvement in group and m is the improvement in elements. Vertical bars in the corrected images look much sharper. The theoretically calculated diffraction limited resolution of the experimental setup is 6.5 microns. The experimental resolution is limited by the size of the pupil P. The best resolution in case of FIGS. 12 (b) and (c) corresponding to element (5,4) in the RTT is about 11 microns which seems to be far from the theoretical limit. This is primarily because of strong local variations of the wavefront across the pupil plane due to the distorted plastic layer causing anisotropic imaging conditions. FIGS. 12(d), 12(e) and 12(f) are the detected phase errors across the apertures in radians in the case of FIGS. 12(a), 12(b) and 12(c) respectively. Note that FIG. 12 (d)-(f) show only the estimation of the phase error that may be present. Unlike the simulation where the reference phase error was known to calculate the residual phase error, in experiment, improvement in image quality is used to judge the best pupil splitting condition.

Figure 13:
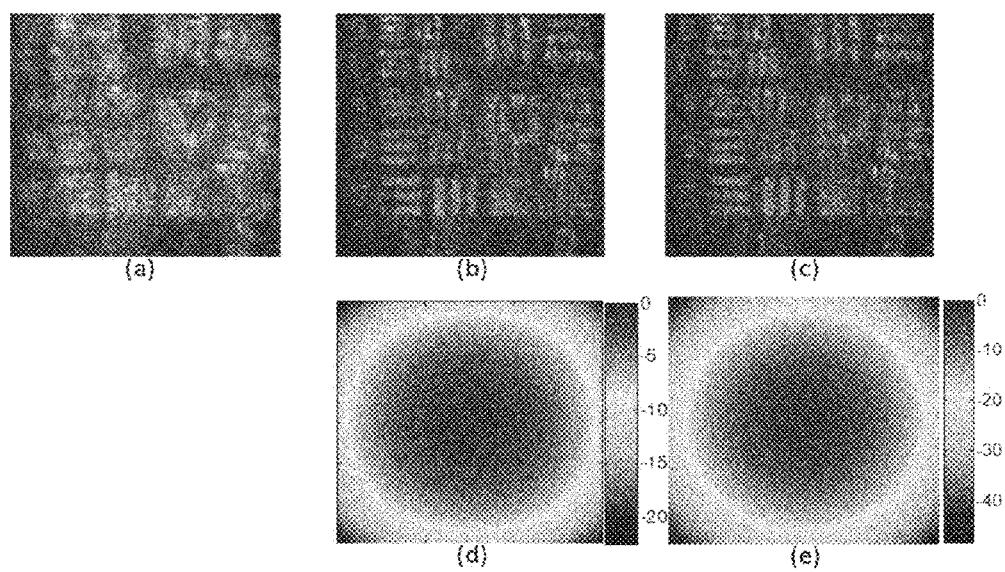
FIG. 13 shows experimental results for the inventive method applied to defocus and refractive index change within the sample.

The effects of defocus and refractive index change within the sample were also investigated. The non-uniform plastic sheet was replaced with a uniform plastic sheet of thickness 1 mm. The presence of the plastic layer causes the image to be defocused. FIG. 13(a) shows the aberrated image obtained where it is barely possible to resolve the (4, 1) bar. FIG. 13(b) shows the phase corrected image result using non-overlapping sub-aperture with K=3. The corresponding estimated phase error in FIG. 13(d) shows the presence of quadratic and $4^{th}$ order terms which is expected due to the presence of defocus and spherical aberration due to change in refractive index within the sample. Since spherical aberration can be balanced with defocus, the two non-overlapping sub-aperture processing technique shown in FIG. 9 was applied to find the effective defocus error. The result is shown in FIG. 13(e). The image obtained with this correction shown in FIG. 13(c) is similar in resolution to image 11(b). The improvement in resolution is clearly evident in these images as the bars up to (5, 6) in FIGS. 13(b) and 11(c) can now be seen which corresponds to the improvement in resolution by a factor of 3.6. Here defocus balances the spherical aberration.

Figure 14:
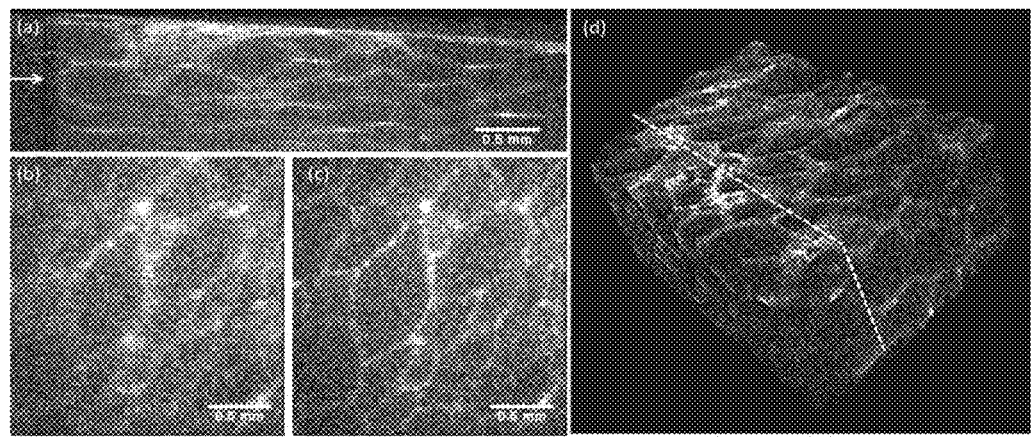
FIG. 14 shows optical coherence images of a grape.

The defocus correction technique using two non-overlapping sub-apertures was applied to the 3D volume image of a grape. The digital refocusing method enables an effective achievement of an extended depth of focus. The first layer of the grape was placed at the focal plane of the microscope objective. Since the theoretical depth of field is only 130 μm in the sample (assuming refractive index of 1.5), the deeper layers are out of focus and appear blurred. FIG. 14 (a) shows a tomogram of the grape sample with an arrow indicating a layer at the depth of 313.5 μm. FIG. 14 (b) shows an enface view of that layer and FIG. 14 (c) shows the defocus corrected image. The lateral resolution improvement is evident as the cell boundaries are clearly visible in the corrected image. FIG. 14(d) shows the corrected 3D volume of data. It is possible to generate movies showing fly throughs in the depth direction of the original and defocus corrected 3D volume images of the grape sample. This illustrates that the same lateral resolution is maintained throughout the depth after defocus correction. In this example, depth of field can be successfully extended by digital defocus correction using just two sub-apertures.

In the case of 3D imaging, the phase error correction can be applied throughout the isoplanatic volume, where the aberration is uniform and the sample has uniform refractive index, using the phase error estimation from a single layer. Furthermore, there is possibility of doing region of interest based phase correction using sub-aperture processing if the aberrations and the sample are not uniform across the volume.

Figure 15:
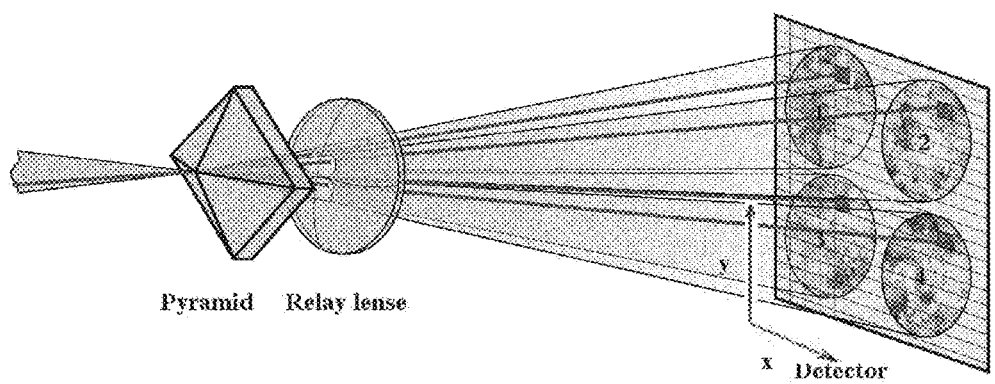
FIG. 15 is a schematic of wavefront detection using a pyramid wavefront sensor as is known in the prior art.

The sub-aperture method described above is conceptually analogous to scene-based Shack-Hartman wavefront sensing combined with coherence-gated wavefront sensing. To illustrate how the coherence-gated, scene-based sub-aperture method may be extended to other known wavefront sensing techniques utilizing sub-apertures and scene based information, a method analogous to a pyramid wavefront sensor is described below and is illustrated in FIG. 15. Firstly the division of the plane in which the aberration should be measured into sub-apertures is performed by applying a different linear phase ramp to each subdivision of the plane. The transformation of the data to the plane containing structures can be performed by transforming the entire plane including all of the sub-apertures in a single transform rather than transforming each sub-aperture separately. Finally the correlation between images should be performed on subsections of the single image produced by transforming the data to the plane containing structures. The number of sub-apertures is flexible. The amount of linear phase ramp applied to each sub-aperture should be sufficient such that the resultant images from each sub-aperture do not overlap significantly.

The sub-aperture correction demonstrated for full field optical interference microscopy acquisition is also applicable to data collected with scanning based interferometric imaging like 'linefield' or 'flying spot' systems. In the full field case, there is an advantage that laterally adjacent points are acquired simultaneously. With a system where scanning is used to build up a volume, there is the potential that motion occurring between scan acquisitions may introduce a phase offset between acquisitions. In this case a phase adjustment may be introduced between each acquisition. The phase adjustment required may be determined by correlation of data acquired at laterally neighboring sensor positions in the spectral domain. This correlation process may be performed on spectra transformed from a bright layer in the object isolated in the spatial domain. A bright, smooth, superficial reflection is ideal for such a reference. This correlation process itself may partially correct or even introduce greater phase errors in the rest of the volume; its purpose however is to remove very high frequency errors. Once the high frequency, per acquisition errors are removed, the technique described above can be used to remove aberrations in the data. In the simplified case of a single b-scan, a sub-aperture phase detection is still possible, however it is active only in a single dimension. By acquiring two orthogonal b-scans, it is possible to gain information about the defocus, spherical and astigmatic (toric) aberration of an eye or other optical system. A more complete view may be assembled from many radial b-scans.

The sub-aperture based phase correction demonstrated for full field optical interference microscopy acquisition is also applicable to data acquired in the related fields of holoscopic imaging systems [22], digital interference holography[28], and Interferometric Synthetic Aperture Microscopy [27] among others. In these cases, the measured data are not represented in a point-to-point imaging from the object to the detector. In an extreme case, the detector is located in the far field relative to the object. The directly detected holoscopic data is in this case is analogous to the standard interferometric data after performing the first Fourier transform of the general method described above and illustrated in FIG. 9 however no depth selection has yet been applied. This example illustrates how the depth selection may be applied at various points in the image processing, for example the acquired data may be split into sub-apertures and then transformed to image planes as well as transformed in the optical frequency direction to separate the depth information. At this point the depth of interest may be isolated and a 2D image selected and correlated according to the method. If the data are recorded at a plane that is defocused to a plane that is neither close to an image plane or close to a Fourier plane, it may be advantageous to digitally propagate the wave to an assumed location of an approximate Fourier plane before splitting it into sub-apertures.

A further instance of holoscopic detection includes the case where the reference radiation is introduced off axis relative to the radiation returning from the object. This arrangement introduces a phase ramp across the recorded data [18]. In this case the data recorded may again be in a Fourier plane or at an intermediate plane. In this case, when images are created by transforming the sub-apertures, each image contains a clearly separated image and complex conjugate image on opposite sides of the zero frequency peak at the center of the image. The locations of the reconstructed image and conjugate image are primarily determined by the phase introduced by the tilt of the reference radiation. Any positional shift in the image due to phase error in the sub-aperture will be introduced in equal and opposite measure in the conjugate image. Therefore to perform correlation between the images of two sub apertures it is critical to crop out the image from a background including the zero-order peak and the complex conjugate image.

The present method can also be extended to aberrometry over a non-isoplanatic full field. i.e., over a region where the aberrations are changing across the field of view of the system. In this instance the correlation between sub-apertures does not result simply in a single peak correlation for the entire sub aperture image, rather the correlation results in a flow field, where each point in the sub-aperture image has a slightly different correspondence or registration to the reference sub-aperture image. This method allows each region of the field of view to have a different phase correction. At this time, it is clear that one could calculate the phase errors for all subregions of the image simultaneously as described above. To reconstruct the image with phase correction, a variable phase correction would need to be applied for plane waves propagated to different directions (image plane locations).

It is also possible to create the full range of spatial frequencies of the Fourier plane using a subset (or cropping) of the image plane. If the subset of the image plane is zero padded to the full size of the image plane prior to transform to the Fourier plane, the spatial frequency sampling density will be similar. If the subset of the image plane is transformed directly or with less zero padding, the spatial frequencies in the Fourier plane will be sampled with less density. This calculated Fourier plane can be divided into sub-apertures and used for wavefront characterization exactly as described using the full image plane data. This method may reduce calculation intensity when an aberration can be assumed to be constant over the image, or may give better isolation to individual fields of view when the aberration is likely to be different across the field of view.

An iterative (but still deterministic) approach may be used to advantage because at each iteration, the quality of the sub images improves and therefore the quality of the sub-aperture correlation may improve until a desired level of correction is achieved. In this case it is logical to increase the order of phasefront correction with the number of iteration cycles, increasing the number of sub apertures and precision of correlations with each iteration. It may also make sense to consider a processing intensive step such as flow estimation only for higher order, more precise calculations.

Because the sub-aperture correlation method is firstly a method to characterize aberrations in an OCT volume, the method has value as an aberrometer such as is used to quantify the aberrations in human eyes, for the recommendation of high end refractive corrections either in for the manufacture of prescription lenses, the selection of intraocular lenses, or as the input to refractive surgical corrections. The method also has value as an aberrometer for materials where traditional aberrometry has been difficult, for example, when multiple reflections make using a Shack-Hartmann sensor difficult [20]. A good aberrometer capable of identifying a specific tissue layer could enable superior adaptive optics microscopy such as for fluorescence measurement, multiphoton fluorescent measurement, femtosecond surgery, or other diagnostic or treatment modalities where high power or resolution is required and where digital phase correction may not be possible. The mouse eye is one such area of scientific interest where it is difficult to isolate aberrations at the specific layers of interest with a traditional wavefront sensor [21].

In a traditional device incorporating a wavefront correction method, an informative device is included to inform the wavefront correction driver of the amount of correction needed. Often such a device is included in a relationship to the wavefront correction method in a manner such that when the wavefront correction is appropriate, the difference state between the measurement made by the informative device, and an ideal measurement state is minimized. If adjustments are made to the wavefront correction method until difference state is minimized the controller can be said to be operating 'closed loop'. Alternatively, a system may operate 'open loop' in which case, a given state of wavefront correction corresponds to a particular input from the informative device, and the system does not rely on an iterative set of feedback and changes to reduce error toward an ideal stable solution.

In a case where a traditional wavefront correction device is improving the beam quality of a delivered beam of optical radiation, the light is usually more concentrated toward a diffraction limited spot size. With a more concentrated spot, greater intensity can be achieved with the same total energy delivered. Especially in the case of non-linear optical processes such as multiphoton fluorescence/absorption, coherent anti-Raman stokes scattering, etc. the desired effect increases at a greater than linear rate with light intensity. In biological tissues, where damage may be accumulated, it is simultaneously critical to keep energy exposures low. Non-linear techniques are often very desirable in thick samples, because the light may only interact absorptively with the sample when the intensity is high, near a focus. Exactly in these samples, it may be difficult to estimate aberrations with traditional techniques. Therefore there is a strong synergy between an optical coherence tomography technique, which can provide a non-invasive preview of a thick, scattering biological sample, and simultaneously provide aberrometry on an optical path to a buried feature; and adaptive optics to phase correct a beam to interrogate or modify the biological sample in the vicinity of the buried feature; especially in the case when delivering a beam for enabling non-linear optical processes.

State-of-the-art wavefront correcting devices include deformable mirrors and liquid crystal modulators, although other devices are possible. The wavefront correcting device is typically placed at or near a pupil plane of the system. A wavefront corrector driver sends signals to actuators on the wavefront correcting device to achieve a variable optical delay across the surface of the device, thereby achieving a variable phase correction across the pupil.

The method described above includes a method to measure the aberration at each depth within a sample and then reconstruct the plane using the observed phase error measurement for that plane. Methods described in references 15, 18, 22 are also easily adapted to include the wavefront error, at least at a single plane, as measured by the currently described method and include it for an efficient calculation of the entire volume. In this case the corrective ability of the method would be limited by the assumption of an isotropic non-aberrating index of refraction within the imaged volume itself. The current method of aberration correction has the advantage that it can calculate aberrations introduced at an arbitrary position within the volume and apply the correction only to layers containing the aberration. Such local phase errors may be corrected at a Fourier plane only for a small patch of the image. To achieve correction over a wider field, local phase errors may be better handled by applying the correction, or a secondary correction at a plane closer to the origin of the aberration. The method described herein adds a deterministic method of finding the phase error, which was missing from previous methods. This deterministic method is better adapted to fast calculation and is more logically implemented in accelerated computation environments such as graphical processor unit (GPU), field programmable gate array (FPGA), or application specific integrated circuit (ASIC) than are previously described iterative methods.

The DFT and FFT are described in a preferred embodiment of the method. Fourier integrals or other means of performing frequency analysis such as wavelet transforms, filter banks, etc. could be used to perform a similar function. Likewise correlation between the sub-apertures is described as a method to compare the displacement of features within images created from sub-aperture data. This should be interpreted as a generic registration technique that finds the spatial relationship between similar distributions in a set of images. The description of the preferred embodiment of the present application includes multiple transformations between spaces related by the Fourier transform. Frequently, transformation to frequency domain is a matter of mathematical or pedagogical convenience and equivalent operations are possible in the alternate domain. In particular, because the correlation operation is equivalent to the multiplication operation (with a sign change equivalent to flipping the array) in the frequency domain, a variety of manipulations may be made to the current preferred embodiment which change the mathematical formalization of the method without changing the overall spirit of the proposed method. [19]

Although various applications and embodiments that incorporate the teachings of the present application have been shown and described in detail herein, those skilled in the art can readily devise other varied embodiments that still incorporate these teachings.

The following references are hereby incorporated by reference:

Patent Literature

U.S. Pat. No. 7,602,501 Ralston et al. "Interferometric Synthetic Aperture Microscopy"
PCT Publication NO. WO 2012/143113 Hillman et al. "Method for Optical Tomography"
US Patent Publication No. 2011/0134436 Podoleanu et al "Method for depth resolved wavefront sensing, depth resolved wavefront sensors and method and apparatus for optical imaging"
U.S. Pat. No. 7,659,993 Feierabend et al. "Method and device for wavefront sensing"
EP Patent No. 1626257 Denk et al. "Method and device for wave-front sensing"

Non-Patent Literature

1. B. C. Platt and R. Shack, "History and principles of Shack Hartmann wavefront sensing", Journal of Refractive Surgery 17, 573-577 (2001).
2. J. C. Beverage, R. V. Shack and M. R. Descour, "Measurement of the three-dimensional microscope point spread function using a Shack-Hartmann wavefront sensor", 205, 61-75 (2002).
3. M. Rueckel, J. A. M. Bucher, W. Denk. "Adaptive wavefront correction in two-photon microscopy using coherence-gated wavefront sensing", Proc Natl Acad Sci USA., 103(46), 17137-17142 (2006).
4. L. A. Poyneer, "Scene-based Shack-Hartmann wave-front sensing: analysis and simulation," Appl. Opt. 42, 5807-5815 (2003).
5. N. Ji, D. E. Milkie and E. Betzig, "Adaptive optics via pupil segmentation for high-resolution imaging in biological tissues", Nature Methods 7, 141-147 (2009).
6. T Haist, J Hafner, M Warber and W Osten, "Scene-based wavefront correction with spatial light modulators", Proc. SPIE 7064, 70640M-70640M-11 (2008).
7. A. E. Tippie and J. R. Fienup, "Sub-Aperture Techniques Applied to Phase-Error Correction in Digital Holography," in *Digital Holography and Three-Dimensional Imaging*, OSA Technical Digest (CD) (Optical Society of America, 2011), paper DMA4. http://www.opticsinfobasc.org/abstract.cfm?URI=DH-2011-DMA4

8. P. Hariharan, *Optical Interferometry* (Academic, 2003).
9. D. Malacara, *Optical Shop Testing* (Wiley, 1992).
10. Markus Rueckel and Winfried Denk, "Properties of coherence-gated wavefront sensing," J. Opt. Soc. Am. A. 24, 3517-3529 (2007).
11. W. Drexler and J. G. Fujimoto, *Optical Coherence Tomography: Technology and Applications* (Springer, 2008)
12. V. N. Mahajan and G. Dai, "Orthonormal polynomials in wavefront analysis: analytical solution," J. Opt. Soc. Am. A. 24, 2994-3016 (2007).
13. M. G. Sicairos, S. T. Thurman, and J. R. Fienup, "Efficient subpixel image registration algorithms," Opt. Lett. 33, 156-158 (2008).
14. S. T. Thurman and J. R. Fienup, "Phase-error correction in digital holography," J. Opt. Soc. Am. A 25, 983-994 (2008).
15. S. G. Adie, et. al., "Computational adaptive optics for broadband optical interferometric tomography of biological tissue," PNAS vol. 109, 7175-7180 (2012).
16. A. E. Tippie, A. Kumar, and J. R. Fienup, "High-resolution synthetic-aperture digital holography with digital phase and pupil correction," Opt. Express 19, 12027-12038 (2011).
17. Y. Nakamura, et al, "High-Speed three dimensional human retinal imaging by line field spectral domain optical coherence tomography" Opt. Express 15(12), 7103 (2007).
18. Franke et al, "High resolution Holoscopy" Proc SPIE 8213, 821324. (2012).
19. Gaskill, Linear Systems, Fourier Transforms, and Optics John Wiley & Sons, Inc. 1978.
20. S. Tuohy et. al., "Depth-resolved wavefront aberrations using a coherence-gated Shack-Hartmann wavefront sensor" Opt. Express 18(4), 3458-3476 (2010).
21. D. P. Biss et. al. "An adaptive optics biomicroscope for mouse retinal imaging" Proc SPIE 6467, 646703 (2007).
22. D. Hillmann et al, "Holoscopy holographic optical coherence tomography" Opt. Letters 36(13), 2390 (2011).
23. M. Feierabend et al. "Coherence-gated wave-front sensing in strongly scattering samples," Opt. Lett. 29, 2255-2257 (2004).
24. M. Pircher and R. J. Zawadzki, "Combining adaptive optics with optical coherence tomography: Unveiling the cellular structure of the human retina in vivo," Expert Rev. Ophthalmol. 2, 1019-1035 (2007).
25. K. Sasaki, K. Kurokawa, S. Makita, and Y. Yasuno, "Extended depth of focus adaptive optics spectral domain optical coherence tomography," Biomed. Opt. Express 3, 2353-2370 (2012).
26. D. Hillmann, G. Franke, C. Lührs, P. Koch, and G. Hüttmann, "Efficient holoscopy image reconstruction," Opt. Express 20, 21247-21263 (2012).
27. U.S. Pat. No. 7,602,501
28. Kim MK "Tomographic three-dimensional imaging of a biological specimen using wavelength-scanning digital interference holography" Optics Express 7(9) 305-310, 2000

The invention claimed is:

1. A method for characterizing a wavefront in collected interferometric data on a sample, wherein the interferometric data is generated using a broad bandwidth light source and wherein the data contains information about a structure within the sample, said method comprising:
generating a beam from the broad bandwidth light source;
dividing the beam into reference and sample arms wherein the sample arm contains the sample to be imaged;
directing the beam to the sample;
combining light scattered from the sample and light returning from the reference arm;
detecting the combined light and generating signals in response thereto;
processing the signals to produce interferometric data;
dividing the interferometric data into lateral subsections at a plane where the wavefront should be characterized;
generating images of the structure or a portion of the structure for at least two of the subsections;
determining a correspondence between the at least two images;
characterizing the wavefront using the correspondence; and
storing, displaying, or using as input to a subsequent process the resulting wavefront characterization.

2. The method as recited in claim 1, wherein the structure is isolated from other structures during the image generating step based on the axial position of the structure.

3. The method as recited in claim 1, wherein the generated images of the structure are limited in the axial dimension using the coherence property of the light source.

4. The method as recited in claim 1, further comprising transforming the data to a plane in the sample containing the structure or a portion of the structure.

5. The method as recited in claim 1, wherein the interferometric data is holoscopic imaging data.

6. The method as recited in claim 5, wherein the holoscopic imaging data is collected in an off-axis configuration.

7. The method as recited in claim 1, wherein the sample is a human eye.

8. The method as recited in claim 1, wherein the subsections overlap.

9. The method as recited in claim 1, further comprising using the characterization of the wavefront as input to a wavefront compensation device to create a compensated wavefront.

10. A method as recited in claim 1, wherein the interferometric imaging data is full-field optical coherence tomography imaging data.

11. A method as recited in claim 1, wherein the interferometric data is line-field optical coherence tomography imaging data.

12. A method as recited in claim 1, wherein the interferometric data is flying spot optical coherence tomography imaging data.

13. A method as recited in claim 1, wherein the broad band light source is a frequency swept laser.

14. A method as recited in claim 1, wherein the characterizing of the wavefront includes a derivation of the local wavefront orientation from the image correspondence between any of the subsection images.

15. A method as recited in claim 1, wherein the characterizing of the wavefront includes a derivation of the wavefront surface from the subsection local wavefront orientation.

16. A method as recited in claim 9, wherein the wavefront compensation device is a deformable mirror.

17. A method as recited in claim 9, wherein the wavefront compensation device is a liquid crystal modulator.

18. A method as recited in claim 1, further comprising using the wavefront characterization to correct the interferometric imaging data and generating an image from the corrected interferometric data.

19. A method as recited in claim 18, further comprising repeating the dividing, generating, determining and characterizing steps until a desired level of correction is achieved.

20. A method as recited in claim 1, wherein the interferometric data is divided into two latera subsections and the wavefront characterization is used to determine defocus.

21. A method as recited in claim 1, further comprising using the characterizing of the wavefront as an input to a manufacturing process.

22. A method as recited in claim 1, further comprising using the characterizing of the wavefront as an input to a surgical process.

23. A method as recited in claim 22, wherein the object is an eye and the surgical process is refractive correction.

24. A method as recited in claim 1, wherein the object is an eye and the characterizing of the wavefront is used as input for custom selection of an intraocular lens.

25. A method as recited in claim 1, wherein the interferometric data is three dimensional.

26. A method as recited in claim 1, wherein the interferometric data is two-dimensional.

27. A method as recited in claim 1, wherein the measurement area on the sample is non-isoplanatic.

28. A method as recited in claim 1, wherein the characterized wavefront is used to compensate for aberrations in a high intensity beam of radiation.

29. A method as recited in claim 1, wherein the characterized wavefront is used to compensate for aberrations in a probe beam for a non-coherent measurement.

30. The method of claim 1, wherein the image correspondence is determined using a flow field where different points in the subsection images have different correspondences.

\* \* \* \* \*

UNITED STATES PATENT AND TRADEMARK OFFICE
CERTIFICATE OF CORRECTION

PATENT NO. : 10,231,616 B2  
APPLICATION NO. : 15/683572  
DATED : March 19, 2019  
INVENTOR(S) : Abhishek Kumar et al.

Page 1 of 1

It is certified that error appears in the above-identified patent and that said Letters Patent is hereby corrected as shown below:

In the Specification

In Column 2, Line 31, delete "(SIM)" and insert -- (SLM) --, therefor.

In Column 8, Line 17, delete "$I_s(\xi,z)=\Delta\xi^2(m\Delta\xi,n\Delta\xi)=I_{m,n}$" and insert -- $I_s(\xi,z)=\Delta\xi^2 I(m\Delta\xi,n\Delta\xi)=I_{m,n}$ --, therefor.

In Column 8, Line 20, delete "in" and insert -- m --, therefor.

In Column 8, Line 21, delete "A×M" and insert -- M×M --, therefor.

In Column 13, Line 22, delete "K=s" and insert -- K=5 --, therefor.

In Column 14, Line 23, delete "Mitotuyo" and insert -- Mitutoyo --, therefor.

Figure 1:
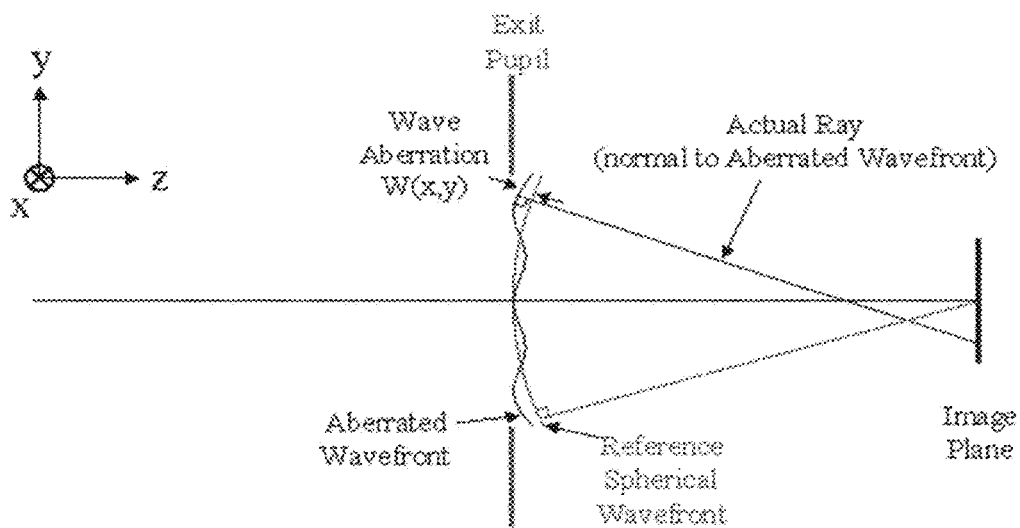
FIG. 1 is a schematic showing an aberrated wavefront relative to an ideal reference wavefront.

In Column 14, Line 26, delete "FIG. 1 (b)" and insert -- FIG. 11 (b) --, therefor.

In Column 15, Line 44, delete "FIG." and insert -- FIGS. --, therefor.

Signed and Sealed this  
Twenty-second Day of September, 2020

Andrei Iancu  
*Director of the United States Patent and Trademark Office*